(12) United States Patent
Yang et al.

(10) Patent No.: US 12,351,603 B2
(45) Date of Patent: Jul. 8, 2025

(54) POLYPEPTIDES AND USES THEREOF

(71) Applicant: SHANXI JINBO BIO-PHARMACEUTICAL CO., LTD., Taiyuan (CN)

(72) Inventors: Xia Yang, Taiyuan (CN); Zhenrui He, Taiyuan (CN)

(73) Assignee: SHANXI JINBO BIO-PHARMACEUTICAL CO., LTD., Taiyuan (CN)

(*) Notice: Subject to any disclaimer, the term of this patent is extended or adjusted under 35 U.S.C. 154(b) by 0 days.

(21) Appl. No.: 18/688,056

(22) PCT Filed: Feb. 23, 2023

(86) PCT No.: PCT/CN2023/077950
§ 371 (c)(1),
(2) Date: Feb. 29, 2024

(87) PCT Pub. No.: WO2024/001242
PCT Pub. Date: Jan. 4, 2024

(65) Prior Publication Data
US 2024/0262868 A1    Aug. 8, 2024

(30) Foreign Application Priority Data

Jun. 29, 2022  (CN) .......................... 202210761804.8

(51) Int. Cl.
| | |
|---|---|
| C07K 14/00 | (2006.01) |
| A61K 8/60 | (2006.01) |
| C12N 15/63 | (2006.01) |
| C12P 19/34 | (2006.01) |

(52) U.S. Cl.
CPC ............ *C07K 14/001* (2013.01); *A61K 8/606* (2013.01); *C12N 15/63* (2013.01); *C12P 19/34* (2013.01); *C07K 2319/20* (2013.01)

(58) Field of Classification Search
CPC ..................................................... A61K 8/64
See application file for complete search history.

(56) References Cited

U.S. PATENT DOCUMENTS

2020/0165319 A1    5/2020   Yang

FOREIGN PATENT DOCUMENTS

| | | |
|---|---|---|
| CN | 103122027 A | 5/2013 |
| CN | 109293783 A | 2/2019 |
| CN | 109593126 A | 4/2019 |
| CN | 113185612 A | 7/2021 |
| CN | 113440431 A | 9/2021 |
| CN | 113476593 A | 10/2021 |
| CN | 113577248 A | 11/2021 |
| CN | 113683679 A | 11/2021 |
| CN | 114920827 A | 8/2022 |
| EP | 3660045 A1 | 6/2020 |

OTHER PUBLICATIONS

International Search Report issued in PCT/CN2023/077950 mailed Apr. 12, 2023. Chinese with English translation.
Liu et al., "Identification and Characterization of Fibronectin-Binding Peptides in Gelatin," Polymers (2022) vol. 14, Article 3757, 16 pages.
Kuivaniemi et al., "Type III collagen (COL3A1): Gene and protein structure, tissue distribution, and associated diseases," Gene (2019) vol. 707, pp. 151-171.
Yao et al., "Design, expression and Characterization of Collagen-Like Proteins Based on the Cell Adhesive and Crosslinking Sequences Derived from Native Collagens," J Biochem (2004) vol. 136, pp. 643-649.

*Primary Examiner* — Suzanne M Noakes

(57) ABSTRACT

Polypeptides and uses thereof are provided. The polypeptide includes an N-terminal sequence and a C-terminal sequence, wherein the N-terminal sequence includes one or more repeating units including the amino acid sequence shown in SEQ ID NO. 1. The use of a human structural material for tissue filling and augmentation is provided in the present disclosure, which is expected to have a wide range of applications in the fields such as breast augmentation, rhinoplasty and mid-face filling as it does not require transplantation from the human body, yet has the natural advantages of using human tissue for filling.

19 Claims, 4 Drawing Sheets
Specification includes a Sequence Listing.

SEQUENCE LISTING

```
Sequence total quantity: 34
SEQ ID NO: 1            moltype = AA  length = 30
FEATURE                 Location/Qualifiers
REGION                  1..30
                        note = repeat region
source                  1..30
                        mol_type = protein
                        organism = synthetic construct
SEQUENCE: 1
GERGAPGFRG PAGPNGIPGE KGPAGERGAP                                          30
```

-continued

```
SEQ ID NO: 2              moltype = AA  length = 9
FEATURE                   Location/Qualifiers
REGION                    1..9
                          note = C
source                    1..9
                          mol_type = protein
                          organism = synthetic construct
SEQUENCE: 2
GAPGPCCGG                                                                  9

SEQ ID NO: 3              moltype = AA  length = 489
FEATURE                   Location/Qualifiers
REGION                    1..489
                          note = AT16
source                    1..489
                          mol_type = protein
                          organism = synthetic construct
SEQUENCE: 3
GERGAPGFRG PAGPNGIPGE KGPAGERGAP GERGAPGFRG PAGPNGIPGE KGPAGERGAP          60
GERGAPGFRG PAGPNGIPGE KGPAGERGAP GERGAPGFRG PAGPNGIPGE KGPAGERGAP         120
GERGAPGFRG PAGPNGIPGE KGPAGERGAP GERGAPGFRG PAGPNGIPGE KGPAGERGAP         180
GERGAPGFRG PAGPNGIPGE KGPAGERGAP GERGAPGFRG PAGPNGIPGE KGPAGERGAP         240
GERGAPGFRG PAGPNGIPGE KGPAGERGAP GERGAPGFRG PAGPNGIPGE KGPAGERGAP         300
GERGAPGFRG PAGPNGIPGE KGPAGERGAP GERGAPGFRG PAGPNGIPGE KGPAGERGAP         360
GERGAPGFRG PAGPNGIPGE KGPAGERGAP GERGAPGFRG PAGPNGIPGE KGPAGERGAP         420
GERGAPGFRG PAGPNGIPGE KGPAGERGAP GERGAPGFRG PAGPNGIPGE KGPAGERGAP         480
GAPGPCCGG                                                                489

SEQ ID NO: 4              moltype = DNA  length = 1467
FEATURE                   Location/Qualifiers
misc_feature              1..1467
                          note = AT16
source                    1..1467
                          mol_type = other DNA
                          organism = synthetic construct
SEQUENCE: 4
ggagaaaggg gggcgcctgg ctttcgtggt ccggcgggtc cgaatggcat tccgggtgaa          60
aagggtcctg ccggtgagcg tggtgctccg ggtgagcgcg cgctccgggt tttccgcggt         120
cccgcgggtc cgaacggcat cccgggagaa aaggccctg ctggcgagcg cggtgcaccg          180
ggcgaacgtg gtgccccggg cttccgtggc ccagcgggtc cgaacggtat tccgggcgag         240
aaaggtccgg caggtgaacg tggtgcgcca ggcgagcgtg gtgcgcctgg tttcagaggc         300
ccagcaggcc caaatggcat ccccggtgag aagggcccag ccggtgagcg cggggcaccg         360
ggtgaacgtg gcgcgcgggt cttcgcggga ccggcgggtc cgaacggcat cccgggtgag         420
aagggtccgg ctggcgagcg tggtgcgccc ggtgaacgtg gtgcaccggg attccgcggc         480
ccggcgggac cgaatggtat tccgggtgag aagggtccgg cgggcgaacg cggagcacca         540
ggcgaacgcg gcgctccggg ctttcgcggt ccggcgggtc cgaatggtat cccgggcgag         600
aagggtcctg ccggtgagcg tggtgccccg ggcgaacgtg gtgccccggg ttttcgtggt         660
ccggcgggtc cgaacggcat tccgggtgaa aagggcccag cggtgagcg tggcgcgcca          720
ggcgagagag gtgccccggg ttttcgtggc ccggcgggtc cgaacggcat cccgggtgag         780
aaaggcccgg cgggcgaacg tggtgcgcca ggcgagagag gtgctccggg tttccgtggc         840
ccggctggtc cgaacggtat tccgggtgaa aagggcccgg cgggcgagcg tggcgcgcca         900
ggtgagcgtg gtgccccagg cttccgtggt ccagctggtc cgaacggtat cccgggtgaa         960
aaaggtccgg cgggtgagcg tggcgcgccg ggtgaacgtg gtgccccagg cttccgcggg        1020
ccggcaggtc ccaacggtat cccgggcgag aaaggtccgg ctggcgagcg aggtgccccg        1080
ggcgaacgtg gcgcgccggt cttccgcggt ccggcaggcc cgaacggtat cccgggcgag        1140
aaaggtccgg caggtgagcg tggtgcgccg ggtgaacgcg gcgctccggg ttttcgtggc        1200
ccggcaggcc caaatggcat tccgggcgaa aaagggcccag cggtgagcg tggtgccccg        1260
ggtgagcgtg gtgcgccggg tttcgcggt ccggcgggtc cgaatggtat tccgggcgaa         1320
aagggcccgg cgggcgagcg tggcgctccg ggcgaacgtg gagcgccagg attccgcggc        1380
ccggcaggac cgaacggcat cccgggagaa aagggcccgg cggtgaacg tggtgcaccg         1440
ggagcgcctg gtccgtgttg cggtggt                                           1467

SEQ ID NO: 5              moltype = AA  length = 498
FEATURE                   Location/Qualifiers
REGION                    1..498
                          note = T16
source                    1..498
                          mol_type = protein
                          organism = synthetic construct
SEQUENCE: 5
GERGAPGFRG PAGPNGIPGE KGPAGERGAP GERGAPGFRG PAGPNGIPGE KGPAGERGAP          60
GERGAPGFRG PAGPNGIPGE KGPAGERGAP GERGAPGFRG PAGPNGIPGE KGPAGERGAP         120
RSGERGAPGF RGPAGPNGIP GEKGPAGERG APGERGAPGF RGPAGPNGIP GEKGPAGERG         180
APGERGAPGF RGPAGPNGIP GEKGPAGERG APGERGAPGF RGPAGPNGIP GEKGPAGERG         240
APRSGERGAP GFRGPAGPNG IPGEKGPAGE RGAPGERGAP GFRGPAGPNG IPGEKGPAGE         300
RGAPGERGAP GFRGPAGPNG IPGEKGPAGE RGAPGERGAP GFRGPAGPNG IPGEKGPAGE         360
RGAPRSGERG APGFRGPAGP NGIPGEKGPA GERGAPGERG APGFRGPAGP NGIPGEKGPA         420
GERGAPGERG APGFRGPAGP NGIPGEKGPA GERGAPGERG APGFRGPAGP NGIPGEKGPA         480
GERGAPRSGP PGPCCGGG                                                      498
```

```
SEQ ID NO: 6             moltype = AA  length = 480
FEATURE                  Location/Qualifiers
REGION                   1..480
                         note = T16c
source                   1..480
                         mol_type = protein
                         organism = synthetic construct
SEQUENCE: 6
GERGAPGFRG PAGPNGIPGE KGPAGERGAP GERGAPGFRG PAGPNGIPGE KGPAGERGAP    60
GERGAPGFRG PAGPNGIPGE KGPAGERGAP GERGAPGFRG PAGPNGIPGE KGPAGERGAP   120
GERGAPGFRG PAGPNGIPGE KGPAGERGAP GERGAPGFRG PAGPNGIPGE KGPAGERGAP   180
GERGAPGFRG PAGPNGIPGE KGPAGERGAP GERGAPGFRG PAGPNGIPGE KGPAGERGAP   240
GERGAPGFRG PAGPNGIPGE KGPAGERGAP GERGAPGFRG PAGPNGIPGE KGPAGERGAP   300
GERGAPGFRG PAGPNGIPGE KGPAGERGAP GERGAPGFRG PAGPNGIPGE KGPAGERGAP   360
GERGAPGFRG PAGPNGIPGE KGPAGERGAP GERGAPGFRG PAGPNGIPGE KGPAGERGAP   420
GERGAPGFRG PAGPNGIPGE KGPAGERGAP GERGAPGFRG PAGPNGIPGE KGPAGERGAP   480

SEQ ID NO: 7             moltype = AA  length = 12
FEATURE                  Location/Qualifiers
source                   1..12
                         mol_type = protein
                         organism = synthetic construct
SEQUENCE: 7
GPAGPNGIPG EK                                                       12

SEQ ID NO: 8             moltype = AA  length = 18
FEATURE                  Location/Qualifiers
source                   1..18
                         mol_type = protein
                         organism = synthetic construct
SEQUENCE: 8
GPAGPNGIPG EKGPAGER                                                 18

SEQ ID NO: 9             moltype = AA  length = 18
FEATURE                  Location/Qualifiers
source                   1..18
                         mol_type = protein
                         organism = synthetic construct
SEQUENCE: 9
GAPGFRGPAG PNGIPGEK                                                 18

SEQ ID NO: 10            moltype = AA  length = 24
FEATURE                  Location/Qualifiers
source                   1..24
                         mol_type = protein
                         organism = synthetic construct
SEQUENCE: 10
GAPGFRGPAG PNGIPGEKGP AGER                                          24

SEQ ID NO: 11            moltype = AA  length = 129
FEATURE                  Location/Qualifiers
source                   1..129
                         mol_type = protein
                         organism = synthetic construct
SEQUENCE: 11
GERGAPGFRG PAGPNGIPGE KGPAGERGAP GERGAPGFRG PAGPNGIPGE KGPAGERGAP    60
GERGAPGFRG PAGPNGIPGE KGPAGERGAP GERGAPGFRG PAGPNGIPGE KGPAGERGAP   120
GAPGPCCGG                                                          129

SEQ ID NO: 12            moltype = DNA  length = 387
FEATURE                  Location/Qualifiers
source                   1..387
                         mol_type = other DNA
                         organism = synthetic construct
SEQUENCE: 12
ggagaaaggg gggcgcctgg ctttcgtggt ccggcgggtc gaatggcat tccgggtgaa     60
aagggtcctg ccggtgagcg tggtgctccg ggtgagcgcg gcgctccggg tttccgcggt   120
cccgcggtc cgaacggcat cccgggagaa aaaggcccag ctggcgagcg cggtgcaccg    180
ggcgaacgtg gtgccccggg cttccgtggc ccagcgggtc cgaacggtat tccgggcgag   240
aaaggtccgg caggtgaacg tggtgcgcca ggcgagcgtg gtgcgcctgg tttcagaggc   300
ccagcaggcc caaatggcat ccccggtgag aagggcccag ccggtgagcg cggggcaccg   360
ggagcgcctg gtccgtgttg cggtggt                                      387

SEQ ID NO: 13            moltype = AA  length = 249
FEATURE                  Location/Qualifiers
source                   1..249
                         mol_type = protein
                         organism = synthetic construct
```

```
SEQUENCE: 13
GERGAPGFRG PAGPNGIPGE KGPAGERGAP GERGAPGFRG PAGPNGIPGE KGPAGERGAP    60
GERGAPGFRG PAGPNGIPGE KGPAGERGAP GERGAPGFRG PAGPNGIPGE KGPAGERGAP   120
GERGAPGFRG PAGPNGIPGE KGPAGERGAP GERGAPGFRG PAGPNGIPGE KGPAGERGAP   180
GERGAPGFRG PAGPNGIPGE KGPAGERGAP GERGAPGFRG PAGPNGIPGE KGPAGERGAP   240
GAPGPCCGG                                                           249

SEQ ID NO: 14           moltype = DNA   length = 747
FEATURE                 Location/Qualifiers
source                  1..747
                        mol_type = other DNA
                        organism = synthetic construct
SEQUENCE: 14
ggagaaaggg gggcgcctgg ctttcgtggt ccggcgggtc cgaatggcat tccgggtgaa    60
aagggtcctg ccggtgagcg tggtgctccg ggtgagcgcg cgctccggg tttccgcggt   120
cccgcgggtc cgaacggcat cccgggagaa aaaggcccag ctggcgagcg cggtgcaccg   180
ggcgaacgtg gtgccccggg cttccgtggc ccagcgggtc cgaacggtat tccgggcgag   240
aaaggtccgg caggtgaacg tggtgcgcca ggcgagcgtg gtgcgcctgg tttcagaggc   300
ccagcaggcc caaatggcat ccccggtgag aagggcccag ccggtgagcg cggggcaccg   360
ggtgaacgtg gcgcgccggg ctttcgcgga ccggcgggtc cgaacggcat cccgggtgag   420
aagggtccgc tggcgagcg tggtgcgccg ggtgaacgtg gtgcaccggg attccgcggc   480
ccggcgggac cgaatggtat tccgggtgag aagggtccgg cggagcacca   540
ggcgaacgcg gcgctccggg ctttcgcggt ccggcgggtc cgaatggtat cccgggcgag   600
aagggtcctg ccggtgagcg tggtgccccg ggcgaacgtg gcgctccggg ttttcgtggt   660
ccggcgggtc cgaacggcat tccgggtgaa aagggcccag cgggtgagcg tggcgcgcca   720
ggagcgcctg gtccgtgttg cggtggt                                       747

SEQ ID NO: 15           moltype = AA   length = 369
FEATURE                 Location/Qualifiers
source                  1..369
                        mol_type = protein
                        organism = synthetic construct
SEQUENCE: 15
GERGAPGFRG PAGPNGIPGE KGPAGERGAP GERGAPGFRG PAGPNGIPGE KGPAGERGAP    60
GERGAPGFRG PAGPNGIPGE KGPAGERGAP GERGAPGFRG PAGPNGIPGE KGPAGERGAP   120
GERGAPGFRG PAGPNGIPGE KGPAGERGAP GERGAPGFRG PAGPNGIPGE KGPAGERGAP   180
GERGAPGFRG PAGPNGIPGE KGPAGERGAP GERGAPGFRG PAGPNGIPGE KGPAGERGAP   240
GERGAPGFRG PAGPNGIPGE KGPAGERGAP GERGAPGFRG PAGPNGIPGE KGPAGERGAP   300
GERGAPGFRG PAGPNGIPGE KGPAGERGAP GERGAPGFRG PAGPNGIPGE KGPAGERGAP   360
GAPGPCCGG                                                           369

SEQ ID NO: 16           moltype = DNA   length = 1107
FEATURE                 Location/Qualifiers
source                  1..1107
                        mol_type = other DNA
                        organism = synthetic construct
SEQUENCE: 16
ggagaaaggg gggcgcctgg ctttcgtggt ccggcgggtc cgaatggcat tccgggtgaa    60
aagggtcctg ccggtgagcg tggtgctccg ggtgagcgcg cgctccggg tttccgcggt   120
cccgcgggtc cgaacggcat cccgggagaa aaaggcccag ctggcgagcg cggtgcaccg   180
ggcgaacgtg gtgccccggg cttccgtggc ccagcgggtc cgaacggtat tccgggcgag   240
aaaggtccgg caggtgaacg tggtgcgcca ggcgagcgtg gtgcgcctgg tttcagaggc   300
ccagcaggcc caaatggcat ccccggtgag aagggcccag ccggtgagcg cggggcaccg   360
ggtgaacgtg gcgcgccggg ctttcgcgga ccggcgggtc cgaacggcat cccgggtgag   420
aagggtccgg ctggcgagcg tggtgcgccg ggtgaacgtg gtgcaccggg attccgcggc   480
ccggcgggac cgaatggtat tccgggtgag aagggtccgg cggcgaacg cggagcacca   540
ggcgaacgcg gcgctccggg ctttcgcggt ccggcgggtc cgaatggtat cccgggcgag   600
aagggtcctg ccggtgagcg tggtgccccg ggcgaacgtg gcgctccggg ttttcgtggt   660
ccggcgggtc cgaacggcat tccgggtgaa aagggcccag cgggtgagcg tggcgcgcca   720
ggcgagagag gtgccccggg ttttcgtggc ccggcgggtc cgaacggcat cccgggtgag   780
aaaggcccgg cgggcgaacg tggtgcgcca ggcgagagag gtgctccggg tttccgtggc   840
ccggctggtc cgaacggtat tccgggtgaa aagggcccgg cgggcgagcg tggcgcgccg   900
ggtgagcgtg gtgccccagg ctttcgtggt ccagctggtc cgaacggtat cccgggtgaa   960
aaaggtccgg cgggtgagcg tggcgcgccg ggtgaacgtg gtgccccagg ctttcgcggg  1020
ccggcaggtc ccaacggtat cccgggcgag aaaggtccgg ctggcgagcg aggtccccg   1080
ggagcgcctg gtccgtgttg cggtggt                                      1107

SEQ ID NO: 17           moltype = AA   length = 609
FEATURE                 Location/Qualifiers
source                  1..609
                        mol_type = protein
                        organism = synthetic construct
SEQUENCE: 17
GERGAPGFRG PAGPNGIPGE KGPAGERGAP GERGAPGFRG PAGPNGIPGE KGPAGERGAP    60
GERGAPGFRG PAGPNGIPGE KGPAGERGAP GERGAPGFRG PAGPNGIPGE KGPAGERGAP   120
GERGAPGFRG PAGPNGIPGE KGPAGERGAP GERGAPGFRG PAGPNGIPGE KGPAGERGAP   180
GERGAPGFRG PAGPNGIPGE KGPAGERGAP GERGAPGFRG PAGPNGIPGE KGPAGERGAP   240
GERGAPGFRG PAGPNGIPGE KGPAGERGAP GERGAPGFRG PAGPNGIPGE KGPAGERGAP   300
GERGAPGFRG PAGPNGIPGE KGPAGERGAP GERGAPGFRG PAGPNGIPGE KGPAGERGAP   360
```

```
GERGAPGFRG PAGPNGIPGE KGPAGERGAP GERGAPGFRG PAGPNGIPGE KGPAGERGAP    420
GERGAPGFRG PAGPNGIPGE KGPAGERGAP GERGAPGFRG PAGPNGIPGE KGPAGERGAP    480
GERGAPGFRG PAGPNGIPGE KGPAGERGAP GERGAPGFRG PAGPNGIPGE KGPAGERGAP    540
GERGAPGFRG PAGPNGIPGE KGPAGERGAP GERGAPGFRG PAGPNGIPGE KGPAGERGAP    600
GAPGPCCGG                                                             609

SEQ ID NO: 18          moltype = DNA  length = 1827
FEATURE                Location/Qualifiers
source                 1..1827
                       mol_type = other DNA
                       organism = synthetic construct
SEQUENCE: 18
ggagaaaggg gggcgcctgg cttcgtggt ccggcgggtc cgaatggcat tccgggtgaa     60
aagggtcctg ccggtgagcg tggtgctccg ggtgagcgcg gcgctccggg tttccgcggt   120
cccgcgggtc cgaacggcat cccgggagaa aaaggcccag ctggcgagcg cggtgcaccg   180
ggcgaacgtg gtgccccggg cttccgtggc ccagcgggtc cgaacggtat tccgggcgag   240
aaaggtccgg caggtgaacg tggtgcgcca ggcgagcgtg gtgcgcctgg tttcagaggc   300
ccagcaggcc caaatggcat ccccggtgag aagggcccag ccggtgagcg cggggcaccg   360
ggtgaacgtg gcgcgccggg cttccgcgga ccggcgggtc cgaacggcat cccgggtgag   420
aagggtccgg ctggcgagcg tggtgcgccg ggtgaacgtg gtgcaccggg attccgcggc   480
ccggcgggac cgaatggtat tccgggtgag aagggtccgg cgggcgaacg cggagcacca   540
ggcgaacgcg gcgctccggg cttccgcggt ccggcgggtc cgaatggtat cccgggcgag   600
aagggtcctg ccggtgagcg tggtgccccg ggcgaacgtg gcgctccggg tttccgtggt   660
ccggcgggtc cgaacggcat tccgggtgaa aagggcccag cggtgagcg tggcgcgcca   720
ggcgagagag gtgccccggg ttccgtggc ccggcgggtc cgaacggcat cccgggtgag   780
aaaggcccgg cgggcgaacg tggtgcgcca ggcgagacg gttccgcggg ttccgcggg    840
ccggctggtc cgaacggtat tccgggtgaa aagggcccgg cgggcgagcg tggcgcgccg   900
ggtgagcgtg gtgccccagg cttccgtggt ccagctggtc cgaacggtat cccgggtgaa   960
aaaggtccgg cgggtgagcg tggcgcgccg ggtgaacgtg gtgccccagg cttccgcggg  1020
ccggcaggtc ccaacggtat cccgggcgag aaaggtccgg ctggcgagcg aggtgccccg  1080
ggcgaacgtg gcgcgccggg cttccgcggt ccggcaggcc cgaacggtat cccgggcgag  1140
aaaggtccgg caggtgagcg tggtgcgccg ggtgaacgcg gcgctccggg ttttcgtggc  1200
ccggcaggcc caaatggcat tccgggcgaa aagggcccag cgggtgagcg tggtgccccg  1260
ggtgagcgcg gtgcgccggg cttccgcggt ccggcgggtc cgaatggtat tccgggcgaa  1320
aagggcccgg cgggcgagcg tggcgctccg ggcgaacgtg gagcgccagg attccgcggt  1380
ccggcaggac cgaacggcat cccgggagaa aagggcccgg cggtgaacg tggtgcaccg   1440
ggagaaaggg gggcgcctgg cttcgtggt ccggcgggtc cgaatggcat tccgggtgaa   1500
aagggtcctg ccggtgagcg tggtgctccg ggtgagcgcg gcgctccggg tttccgcggt  1560
cccgcgggtc cgaacggcat cccgggagaa aaaggcccag ctggcgagcg cggtgcaccg  1620
ggcgaacgtg gtgccccggg cttccgtggc ccagcgggtc cgaacggtat tccgggcgag  1680
aaaggtccgg caggtgaacg tggtgcgcca ggcgagcgtg gtgcgcctgg tttcagaggc  1740
ccagcaggcc caaatggcat ccccggtgag aagggcccag ccggtgagcg cggggcaccg  1800
ggagcgcctg gtccgtgttg cggtggt                                      1827

SEQ ID NO: 19          moltype = AA  length = 8
FEATURE                Location/Qualifiers
source                 1..8
                       mol_type = protein
                       organism = synthetic construct
SEQUENCE: 19
GPAGERGA                                                              8

SEQ ID NO: 20          moltype = AA  length = 12
FEATURE                Location/Qualifiers
source                 1..12
                       mol_type = protein
                       organism = synthetic construct
SEQUENCE: 20
GFRGPAGPNG IP                                                        12

SEQ ID NO: 21          moltype = AA  length = 15
FEATURE                Location/Qualifiers
source                 1..15
                       mol_type = protein
                       organism = synthetic construct
SEQUENCE: 21
GERGAPGERG APGFR                                                     15

SEQ ID NO: 22          moltype = AA  length = 21
FEATURE                Location/Qualifiers
source                 1..21
                       mol_type = protein
                       organism = synthetic construct
SEQUENCE: 22
EKGPAGERGA PGERGAPGFR G                                              21

SEQ ID NO: 23          moltype = AA  length = 10
FEATURE                Location/Qualifiers
source                 1..10
```

```
                              mol_type = protein
                              organism = synthetic construct
SEQUENCE: 23
GPNGIPGEKG                                                              10

SEQ ID NO: 24                 moltype = AA   length = 13
FEATURE                       Location/Qualifiers
source                        1..13
                              mol_type = protein
                              organism = synthetic construct
SEQUENCE: 24
KGPAGERGAP GER                                                          13

SEQ ID NO: 25                 moltype = AA   length = 16
FEATURE                       Location/Qualifiers
source                        1..16
                              mol_type = protein
                              organism = synthetic construct
SEQUENCE: 25
PAGPNGIPGE KGPAGE                                                       16

SEQ ID NO: 26                 moltype = AA   length = 22
FEATURE                       Location/Qualifiers
source                        1..22
                              mol_type = protein
                              organism = synthetic construct
SEQUENCE: 26
AGPNGIPGEK GPAGERGAPG ER                                                22

SEQ ID NO: 27                 moltype = AA   length = 10
FEATURE                       Location/Qualifiers
source                        1..10
                              mol_type = protein
                              organism = synthetic construct
SEQUENCE: 27
ERGAPGFRGP                                                              10

SEQ ID NO: 28                 moltype = AA   length = 13
FEATURE                       Location/Qualifiers
source                        1..13
                              mol_type = protein
                              organism = synthetic construct
SEQUENCE: 28
RGAPGERGAP GFR                                                          13

SEQ ID NO: 29                 moltype = AA   length = 15
FEATURE                       Location/Qualifiers
source                        1..15
                              mol_type = protein
                              organism = synthetic construct
SEQUENCE: 29
GPAGPNGIPG EKGPA                                                        15

SEQ ID NO: 30                 moltype = AA   length = 23
FEATURE                       Location/Qualifiers
source                        1..23
                              mol_type = protein
                              organism = synthetic construct
SEQUENCE: 30
NGIPGEKGPA GERGAPGERG APG                                               23

SEQ ID NO: 31                 moltype = AA   length = 10
FEATURE                       Location/Qualifiers
source                        1..10
                              mol_type = protein
                              organism = synthetic construct
SEQUENCE: 31
PAGPNGIPGE                                                              10

SEQ ID NO: 32                 moltype = AA   length = 14
FEATURE                       Location/Qualifiers
source                        1..14
                              mol_type = protein
                              organism = synthetic construct
SEQUENCE: 32
GFRGPAGPNG IPGE                                                         14

SEQ ID NO: 33                 moltype = AA   length = 18
FEATURE                       Location/Qualifiers
```

```
                              -continued
source              1..18
                    mol_type = protein
                    organism = synthetic construct
SEQUENCE: 33
RGAPGERGAP GFRGPAGP                                                 18

SEQ ID NO: 34       moltype = AA  length = 24
FEATURE             Location/Qualifiers
source              1..24
                    mol_type = protein
                    organism = synthetic construct
SEQUENCE: 34
PGERGAPGFR GPAGPNGIPG EKGP                                          24
```

POLYPEPTIDES AND USES THEREOF

This application is a U.S. National Phase Application under 35 U.S.C. § 371 of International Application No. PCT/CN2023/077950, filed Feb. 23, 2023, which claims priority to Chinese Patent Application No. 202210761804.8, entitled "POLYPEPTIDES AND USES THEREOF", filed Jun. 29, 2022, each of which is incorporated herein by reference in its entirety.

SEQUENCE LISTING

The instant application contains a Sequence Listing which has been submitted electronically in XML file format and is hereby incorporated by reference in its entirety. Said XML copy, created on Jan. 17, 2024, is named LS-SHANXI-7000US_SL.xml and is 40,985 bytes in size.

TECHNICAL FIELD

The present disclosure belongs to the technical field of synthetic biology, and specifically relates to collagen polypeptides, a human body structural material which can be used for tissue filling and augmentation.

BACKGROUND OF THE INVENTION

Due to genetic factors, nutritional status, age factors, etc., some people will have facial structural defects such as temporal depression, nasal base depression, short and retracted chin, depressed nasal bridge. Some women will also have problems such as breast dysplasia or ptosis and atrophy, which seriously affect the aesthetics. With the continuous improvement of people's living standards and the opening up of their mindset, more and more people begin to pay attention to the cosmetic surgery. At present, a filling surgery can be used to improve the appearance and figure of women, in order to obtain a high straight and beautiful nose shape, a flat and smooth face, and full and round breasts. The filling surgery at the present stage can be mainly divided into prosthesis implantation surgery, autologous tissue transplantation surgery, and injection filling surgery.

In the early breast augmentation surgery and rhinoplasty, silica gel prostheses are often used as implants, because silica gel has a good tissue compatibility, no carcinogenicity, no mutagenicity, no teratogenicity and no other problems, and its tear resistance, hardness, elastic retraction force and other aspects are relatively satisfactory. It has the advantages of easy operation, beautiful appearance, immediate effect, etc. However, due to the static electricity on the surface of the silica gel prosthesis, it is easy to absorb some dust or cilia, which can easily lead to wound infection and will also cause some complications after surgery. For example, complications such as obvious scars near breast augmentation incision, a long distance between breasts, difficulty in lifting, prosthesis rupture, leakage, and capsular contracture may occur, and the probability of prosthesis contracture and rupture increases with the prolongation of prosthesis implantation time. Rhinoplasty is prone to problems such as light transmission of the prosthesis, poor tissue compatibility, hard material, poor touch after implantation, easy displacement, etc. Complications such as nasal swelling, nasal tip dermatitis, and excessive subcutaneous tension may be caused, and the nasal dorsum may not be supported.

With the development of plastic surgery techniques, autologous tissue transplantation has played an increasingly important role in cosmetic surgery. Among them, autologous fat transplantation for breast augmentation, rhinoplasty, and mid-face filling is to transplant the fat particles from the richer parts of the body to desired parts. The autologous fat transplantation is usually performed by injection, which has advantages of less pain, less surgical trauma, shorter time-consuming, no obvious scar in the surgical area, and quick postoperative recovery. The filler for autologous fat transplantation is derived from recipients themselves and has the following properties: is biocompatible and has no immune rejection response after transplantation; will not affect the recipients' own breast or nasal functions; has an excellent fusion capability, and is not easy to shift; fewer postoperative complications; and can also slim down and shape up the recipients. However, the traditional fat collection and injection techniques have shortcomings such as high absorption rate and low survival rate, and excessive one-time transplantation can also cause complications such as breast nodules, so multiple fat transplantations are often required to achieve the desired effect. In addition to autologous fat, autologous cartilage can also be used as a raw material for rhinoplasty and mid-face filling. The autologous cartilage has similar advantages to autologous fat, but it will produce autologous distortion and deformation, which will have a greater impact on the subsequent filling effect.

The injection filling is a surgical procedure in which artificial chemicals are filled into breast or facial defects by injection. Among them, artificial fat is the most commonly used injection filling material, and its chemical composition is hydrophilic polyallylamine hydrogel, which is often used in breast augmentation, but it has been found to cause many complications and adverse reactions in subsequent long-term applications. The hydrogel will contain toxic heavy metals during the production process, which are easily absorbed and accumulated by the human body through the skin and mucous membranes, causing poisoning. It also has varying degrees of toxic and side effects on cells and kidneys. After the injection, the hydrogel will cause complications such as lumps or induration in the breast, pain, bilateral breast asymmetry, infection, lactation mastitis, aseptic inflammation, breast ulceration and perforation, displacement of the injected material, and limited movement of upper limb. Some patients have several complications coexisted.

With the development of modern technology, recombinant collagen can be produced by genetic engineering technology, but the collagen currently on the market is mainly obtained through mutation of the sequence of human collagen, which belongs to collagen-like protein and still has certain immunogenicity. Such collagen still needs to be mixed with a cross-linking agent to prepare a gel product in order to achieve its biomechanical properties and complete tissue augmentation and filling. However, the use of the cross-linking agent often leads to unobservable side effects and reactions to foreign materials produced as collagen with low immunogenicity and non-toxicity is used. Therefore, there is an urgent need in the field to find a humanized collagen having no exogenous gene sequences, non-immunogenicity, high biocompatibility, and the ability to cross-link on its own, and which can be used as a structural material for tissue filling and augmentation.

SUMMARY OF THE INVENTION

The inventors have conducted long-term research on humanized collagen, and discovered a variety of type III collagen polypeptides in Chinese patent applications CN201210482543.2 and CN201811438582.6. The present inventors further conducted research on these discovered collagen polypeptides, and found that these collagen polypeptides cannot form gels by themselves at a low temperature. Surprisingly, the inventors added small peptide segments to the previously discovered collagen polypeptides, enabling the formed collagen polypeptides to form gels at the low temperature. The gels of the present disclosure may be free of a cross-linking agent.

In one aspect, the present disclosure provides a polypeptide comprising an N-terminal sequence and a C-terminal sequence, wherein the N-terminal sequence comprises one or more repeating units comprising the amino acid sequence shown in SEQ ID NO:1, and the C-terminal sequence is the amino acid sequence shown in SEQ ID NO:2. The amino acid sequence of SEQ ID NO:1 is gergapgfrgpagpngipgekgpagergap. The amino acid sequence of SEQ ID NO:2 is gapgpccgg.

In one embodiment, the repeating unit may be an amino acid sequence obtained after mutation (substitution, insertion, deletion or addition) of one or more amino acid residues in the amino acid sequence of SEQ ID NO:1.

In one embodiment, the C-terminal sequence may be an amino acid sequence obtained after mutation (substitution, insertion, deletion or addition) of one or more amino acid residues in the amino acid sequence of SEQ ID NO:2.

In one embodiment, the number of the repeating unit is 1-20.

In one embodiment, the number of the repeating unit is 2, 3, 4, 5, 6, 7, 8, 9, 10, 11, 12, 13, 14, 15, 16, 17, 18, 19 or 20.

In one embodiment, the N-terminal sequence and the C-terminal sequence are directly linked or separated by one or more amino acid residues.

In one embodiment, each repeating unit is directly linked or separated by one or more amino acid residues;

In one embodiment, the polypeptide comprises an amino acid sequence of SEQ ID NO:3 or an amino acid sequence obtained after mutation (substitution, insertion, deletion or addition) of one or more amino acid residues in the amino acid sequence of SEQ ID NO:3.

In one embodiment, in the case of a mutation in the polypeptide sequences, the obtained polypeptides retain the functions of the present disclosure, such as cell adhesion, the ability to form a gel by itself, and the like.

In one aspect, the present disclosure provides a polynucleotide encoding the polypeptide described herein.

In one embodiment, the polynucleotide comprises the nucleotide sequence shown in SEQ ID NO:4.

In one aspect, the present disclosure provides a nucleic acid comprising a polynucleotide herein.

In one embodiment, the nucleic acid further comprises nucleotides encoding a purification tag, e.g. an His tag, a GST tag, an MBP tag, a SUMO tag, or a NusA tag.

In one embodiment, the nucleic acid further comprises nucleotides encoding a leader sequence.

In one aspect, the present disclosure provides a vector comprising the polynucleotide or the nucleic acid herein. In one embodiment, the vector is an expression vector. In one embodiment, the vector comprises an expression control element, such as a promoter, a terminator and/or an enhancer, operably linked to the polynucleotide or the nucleic acid.

In one aspect, the present disclosure provides a host cell comprising the polynucleotide, the nucleic acid or the vector herein.

In one embodiment, the host cell is a bacterial, fungal or animal cell. In one embodiment, the bacterium is *E. coli*. In one embodiment, the fungus is a yeast, such as *Saccharomyces cerevisiae*.

In one aspect, the present disclosure provides a method of producing the polypeptide comprising:
(1) culturing the host cell described herein under a suitable culture condition;
(2) harvesting the host cell and/or the culture medium comprising the polypeptide;
(3) purifying the polypeptide.

In one aspect, the present disclosure provides a composition comprising the polypeptide described herein. The composition may be a composition for tissue filling and/or augmentation.

In one aspect, the present disclosure provides a gel comprising or prepared from the polypeptide described herein. In one embodiment, the gel does not comprise a cross-linking agent. In one embodiment, the gel herein is a human body structural material for use in tissue filling and/or augmentation.

In another aspect, the present disclosure provides a method of preparing a gel comprising the step of storing the polypeptide described herein at a low temperature.

In one embodiment, the low temperature is a temperature ranging from 2 to 8° C. In one embodiment, the low temperature is 2° C., 3° C., 4° C., 5° C., 6° C., 7° C. or 8° C.

In one embodiment, the method of the present disclosure includes the step of storing the polypeptide solution. Preferably, the polypeptide solution is a sodium chloride solution of the polypeptide. The solution may be 50-500 mM NaCl, e.g. 100 mM, 150 mM, 200 mM, 250 mM, 300 mM, 350 mM, 400 mM or 450 mM. In one embodiment, the pH of the sodium chloride solution is above 6, e.g. 6.5, 7, 7.5, 8.0, 8.5, 9 or 9.5.

In yet another aspect, the present disclosure provides the use of the polypeptide, the polynucleotide, the nucleic acid, the host cell, the composition or the gel described herein for increasing cell adhesion or for use as tissue filling and augmentation. For example, the polypeptide, the polynucleotide, the nucleic acid, the host cell, the composition or the gel herein can be used for breast augmentation, rhinoplasty and/or facial filling.

Advantages of the present disclosure include:
1. The present disclosure successfully synthesized a recombinant type III humanized collagen gel at low-temperature for the first time, and the amino acid sequence of the collagen is all derived from the human body itself, without exogenous amino acid sequence;
2. The recombinant type III humanized collagen prepared by the present disclosure can undergo a cross-linking reaction to form a low-temperature gel without the participation of an exogenous cross-linking agent, and has no biological toxicity;
3. The recombinant type III humanized collagen gel prepared at a low-temperature by the present disclosure belongs to humanized collagen, which has good tissue filling and augmentation effects, and has no immune response and strong tissue compatibility when applied to the human body, and can be injected directly into the human body as a structural material;
4. The method of biosynthesizing the recombinant type III humanized collagen low-temperature gel in the present disclosure can be industrially and stably produced on a large scale;

5. The present disclosure provides the use of a human body structural material for tissue filling and augmentation, which is expected to be widely used in fields such as breast augmentation, rhinoplasty and mid-face filling, because it does not require transplantation from the human body but has the natural advantage of human tissue filling.

DETAILED DESCRIPTION

Figure 1:
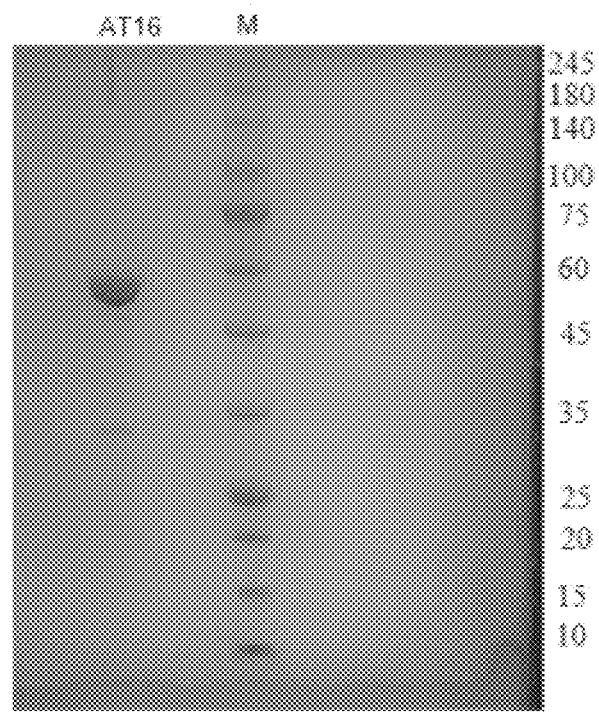
FIG. 1: Electrophoresis detection results of the purified recombinant type III humanized collagen AT16.

In order to make the purpose, technical solutions and advantages of the present disclosure clearer, the technical solutions in the embodiments of the present disclosure will be clearly and completely described below in conjunction with the embodiments of the present disclosure. It will be obvious that the described embodiments are a part of the embodiments of the present disclosure, but not all of the embodiments. Based on the embodiments of the present disclosure, all other embodiments obtained by those of ordinary skill in the art without making creative work fall within the scope of protection of the present disclosure.

The inventors have conducted long-term research on humanized collagen, and discovered a variety of type III collagen polypeptides in Chinese patent applications CN201210482543.2 and CN201811438582.6. The present inventors have further conducted research on these discovered collagen polypeptides, and found that these collagen polypeptides cannot form gels by themselves at a low temperature. Surprisingly, the inventors added small peptide segments to the previously discovered collagen polypeptides, enabling the formed collagen polypeptides to form gels at the low temperature. The gels of the present disclosure may be free of a cross-linking agent. The amino acid sequence of the functional region of the recombinant type III humanized collagen AT16 screened out is: gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gergapgfrgpagpngipgekgpagergap gapgpccgg (SEQ ID NO:3). The underlined amino acid sequence part is a region for ligation to the amino acid sequences of the patent CN201811438582.6 and providing a new functional region.

As used herein, a "polypeptide" refers to a plurality of amino acid residues linked by a peptide bond. As used herein, with respect to a polypeptide or a specific amino acid sequence, the "C-terminal" and "N-terminal" refer to the position relative to the polypeptide or the particular amino acid sequence, specifically at the carboxy-terminal or amino-terminal direction of the polypeptide or the particular amino acid sequence.

Herein, from the N-terminus to the C-terminus, a polypeptide may comprise an N-terminal sequence and a C-terminal sequence. The N-terminal sequence may comprise one or more repeating units comprising the amino acid sequence shown in SEQ ID NO:1 or the amino acid sequence obtained after mutation (substitution, addition, insertion or deletion) of one or more amino acid residues in the amino acid sequence shown in SEQ ID NO:1. The number of the repeating unit may be 1-20. For example, the number of the repeating unit is 2, 3, 4, 5, 6, 7, 8, 9, 10, 11, 12, 13, 14, 15, 16, 17, 18, 19 or 20. In particular, the mutation may be a substitution, such as a conservative amino acid substitution. The amino acid sequence of SEQ ID NO:1 is gergapgfrgpagpngipgekgpagergap. In the N-terminal sequence, each repeating unit may be directly linked or separated by one or more amino acid residues.

The C-terminal sequence may be the amino acid sequence shown in SEQ ID NO:2 or the amino acid sequence obtained after mutation (substitution, addition, insertion or deletion) of one or more amino acid residues in the amino acid sequence shown in SEQ ID NO:2. In particular, the mutation may be a substitution, such as a conservative amino acid substitution. The amino acid sequence of SEQ ID NO:2 is gapgpccgg. The N-terminal sequence and the C-terminal sequence may be directly linked or may be separated by one or more amino acid residues, for example 2-10 amino acid residues. For example, the N-terminal and the C-terminal sequence may be separated by 3, 4, 5, 6, 7, 8 or 9 amino acid residues.

In the case of a mutation in the polypeptide sequence or the presence of a spacer sequence, the obtained polypeptide retains the functions of the present disclosure, such as cell adhesion, the ability to form a gel by itself, and the like.

The polypeptide of the present disclosure may be synthetic or may be expressed recombinantly. In the case of recombinant expression, the polypeptide of the present disclosure may be encoded by a polynucleotide. The polynucleotide can be codon-optimized for the host cell in which it is expressed. The polynucleotide encoding the polypeptide may be operably linked to an expression control element, such as a promoter, a terminator and/or an enhancer, to constitute a nucleic acid, or an expression cassette. The nucleic acid may also comprise nucleotides encoding a purification tag, e.g. an His tag, a GST tag, an MBP tag, a SUMO tag, or a NusA tag, or nucleotides encoding a leader sequence to facilitate purification or secretion of the polypeptide.

As used herein, the term "vector" is a nucleic acid delivery vehicle into which a polynucleotide can be inserted. When the vector enables the expression of the protein encoded by the inserted polynucleotide, the vector is called an expression vector. The vector can be introduced into a host cell by transformation, transduction or transfection, so that the genetic material elements it carries can be expressed in the host cell. The vector is well known to those skilled in the art, including but not limited to: a plasmid; a phagemid; a cosmid; an artificial chromosome, such as yeast artificial chromosome (YAC), a bacterial artificial chromosome (BAC) or a P1-derived artificial chromosome (PAC); a phage such as a λ phage or a M13 phage, and an animal viruses and so on. The vector may contain a variety of elements that control expression, including, but not limited to, promoter sequences, transcription initiation sequences, enhancer sequences, selection elements, and reporter genes. In addition, the vector may also contain a replication initiation site. The vector may comprise the nucleic acid of the present disclosure to facilitate introduction into a cell for expression. The vector may comprise an expression control element, such as a promoter, a terminator and/or an enhancer, operably linked to the nucleic acid.

As used herein, the term "host cell" is a cell into which a nucleic acid molecule has been introduced by molecular biology techniques. These techniques include transfection with viral vectors, transformation with plasmid vectors, and accelerated introduction of naked DNA by electroporation, lipofection, and particle guns. The host cell may be eukaryotic or prokaryotic. For example, the eukaryotic cell is a yeast cell, an animal cell and/or an insect cell. The prokaryotic cell may be an *E. coli* cell.

The present disclosure also provides a method of producing the polypeptide, which comprises: (1) culturing the host cell herein under a suitable culture condition; (2) harvesting the host cell and/or the culture medium comprising the polypeptide; and (3) purifying the polypeptide. The method of the present disclosure may include the step of digesting the tag via an enzyme.

The polypeptide of the present disclosure may be prepared into a composition or a kit. The composition or the kit may be a composition or a kit for tissue filling and/or augmentation. The composition or the kit may also comprise an auxiliary substance. The composition of the present disclosure may be a gel comprising the polypeptide described herein. The gel may be produced autonomously from the polypeptide described herein, without a cross-linking agent. The composition of the present disclosure, particularly the gel, is a human body structural material, e.g. useful for tissue filling and/or augmentation. The gel of the present disclosure may be prepared by a simple method. For example, a method of making a gel may comprise the step of storing the polypeptide described herein at a low temperature. The polypeptide of the present disclosure may achieve self-gelation at a low temperature. The low temperature may be a temperature of 2-8° C., such as 2° C., 3° C., 4° C., 5° C., 6° C., 7° C. or 8° C. The methods of the present disclosure may comprise the step of storing a polypeptide solution. Preferably, the polypeptide solution is an aqueous sodium chloride solution of the polypeptide. The sodium chloride solution may be a 50 mM-500 mM solution. For example, the sodium chloride solution may be 100 mM, 150 mM, 200 mM, 250 mM, 300 mM, 350 mM, 400 mM, or 450 mM. In one embodiment, the pH of the sodium chloride solution is above 6, e.g. 6.5, 7, 7.5, 8.0, 8.5, 9 or 9.5. The concentration of the polypeptide in the solution may be greater than 5 mg/mL, or greater than 10 mg/mL, for example, may be 10 mg/mL, 15 mg/mL, 20 mg/mL, 30 mg/mL, 40 mg/mL, 50 mg/mL, 60 mg/mL, 70 mg/mL, 80 mg/mL, 90 mg/mL, 100 mg/mL, 200 mg/mL, 300 mg/mL or greater concentrations.

EXAMPLES

The following Examples are provided to illustrate the present disclosure. It should be understood by those skilled in the art that the Examples are merely illustrative and not limiting. The present disclosure is limited only by the scope of the appended claims.

Example 1: Construction and Expression of the Recombinant Type III Humanized Collagen Gel 1. A large-scale functional region screening and assembly were performed to obtain the gene fragments of interest for the recombinant type III humanized collagen. The amino acid sequence of AT16 is: gergapgfrgpagpngipgekgpagergapgergapgfrgpagpngipgekgpagergapgergapgfrgpa gpngipgekgpagergapgergapgfrgpagpngipgekgpagergapgergapgfrgpagpngipgekgpagergapgergapgfrgpagpngipgekgpagergapgergapgfrgpagpngipgekgpagergapgergapgfrgpagpngipgekgpagergapgerga pgfrgpagpngipgekgpagergapgergapgfrgpagpngipgekgpagergapgergapgfrgpagpngi pgekgpagergapgergapgfrgpagpngipgekgpagergapgergapgfrgpagpngipgekgpagerg apgergapgfrgpagpngipgekgpagergapgergapgfrgpagpngipgekgpagergapgergapgfrg pagpngipgekgpagergapgergapgfrgpagpngipgekgpagergapgapgpccgg (SEQ ID NO: 3). In the present disclosure, codon optimization was performed for the codon of *E. coli*, and the optimized base sequence is (SEQ ID NO: 4)
GGAGAAAGGGGGGCGCCTGGCTTTCGTGGTCCGGCGGGTCCGAATGGCAT

TCCGGGTGAAAAGGGTCCTGCCGGTGAGCGTGGTGCTCCGGGTGAGCGCG

GCGCTCCGGGTTTCCGCGGTCCCGCGGGTCCGAACGGCATCCCGGGAGAA

AAAGGCCCAGCTGGCGAGCGCGGTGCACCGGGCGAACGTGGTGCCCCGGG

CTTCCGTGGCCCAGCGGGTCCGAACGGTATTCCGGGCGAGAAAGGTCCGG

CAGGTGAACGTGGTGCGCCAGGCGAGCGTGGTGCGCCTGGTTTCAGAGGC

CCAGCAGGCCCAAATGGCATCCCCGGTGAGAAGGGCCCAGCCGGTGAGCG

CGGGGCACCGGGTGAACGTGGCGCGCCGGGCTTTCGCGGACCGGCGGGTC

CGAACGGCATCCCGGGTGAGAAGGGTCCGGCTGGCGAGCGTGGTGCGCCG

GGTGAACGTGGTGCACCGGGATTCCGCGGCCCGGCGGGACCGAATGGTAT

TCCGGGTGAGAAGGGTCCGGCGGGCGAACGCGGAGCACCAGGCGAACGCG

GCGCTCCGGGCTTTCGCGGTCCGGCGGGTCCGAATGGTATCCCGGGCGAG

AAGGGTCCTGCCGGTGAGCGTGGTGCCCCGGGCGAACGTGGCGCTCCGGG

TTTTCGTGGTCCGGCGGGTCCGAACGGCATTCCGGGTGAAAAGGGCCCAG

CGGGTGAGCGTGGCGCGCCAGGCGAGAGAGGTGCCCCGGGTTTTCGTGGC

CCGGCGGGTCCGAACGGCATCCCGGGTGAGAAAGGCCCGGCGGGCGAACG

TGGTGCGCCAGGCGAGAGAGGTGCTCCGGGTTTCCGTGGCCCGGCTGGTC

CGAACGGTATTCCGGGTGAAAAGGGCCCGGCGGGCGAGCGTGGCGCGCCG

GGTGAGCGTGGTGCCCCAGGCTTTCGTGGTCCAGCTGGTCCGAACGGTAT

CCCGGGTGAAAAGGTCCGGCGGGTGAGCGTGGCGCGCCGGGTGAACGTG

GTGCCCCAGGCTTCCGCGGCCGGCAGGTCCCAACGGTATCCCGGGCGAG

AAAGGTCCGGCTGGCGAGCGAGGTGCCCCGGGCGAACGTGGCGCGCCGGG

CTTCCGCGGTCCGGCAGGCCCGAACGGTATCCCGGGCGAGAAAGGTCCGG

-continued
CAGGTGAGCGTGGTGCGCCGGGTGAACGCGGCGCTCCGGGTTTTCGTGGC

CCGGCAGGCCCAAATGGCATTCCGGGCGAAAAAGGCCCAGCGGGTGAGCG

TGGTGCCCCGGGTGAGCGCGGTGCGCCGGGTTTCCGCGGTCCGGCGGGTC

CGAATGGTATTCCGGGCGAAAAAGGCCCGGCGGGCGAGCGTGGCGCTCCG

GGCGAACGTGGAGCGCCAGGATTCCGCGGCCCGGCAGGACCGAACGGCAT

CCCGGGAGAAAAGGGCCCGGCGGGTGAACGTGGTGCACCGGGAGCGCCTG

GTCCGTGTTGCGGTGGT

2. The synthetic gene fragment was inserted into a pET-28a-Trx-His expression vector to obtain a recombinant expression plasmid.
3. The successfully constructed expression plasmid was transformed into *E. coli* competent cells BL21 (DE3). The specific process is as follows. (1) The *E. coli* competent cells BL21 (DE3) were taken out from the ultra-low temperature refrigerator and placed on ice, and when half-thawed, 2 μl of the plasmid to be transformed was taken and added into the *E. coli* competent cells BL21 (DE3), with mixing slightly 2-3 times. (2) The mixture was placed on ice for 30 min, then heat shocked in a water bath at 42° C. for 45-90 s, and taken out and placed in ice bath on ice for 2 min. (3) The mixture was transferred into a biosafety cabinet, and 700 μl of liquid LB medium was added, and then cultured at 37° C., 220 rpm for 60 min. (4) 200 μl of the bacterial solution was taken and evenly spread on the LB plate containing kanamycin sulfate. (5) The plate was cultured in an incubator at 37° C. for 15-17 h until colonies of uniform size grow out.
4. The single colony of optimized genetically engineered *E. coli* was pick out and placed in LB liquid medium containing kanamycin, cultured at 37° C., 220 rpm for 5 hours, then cooled down to 16° C., and added with IPTG to a final concentration of 0.5 mM for induction. After incubation for 16 hours, the culture was centrifuged at 6000 rpm, 4° C. for 12 min to collect the bacterial cells.
5. The recombinant humanized type III collagen was purified and enzymatically digested, and the specific process is as follows. (1) The bacteria were resuspended in Tris buffer (25 mM Tris, 200 mM NaCl, 20 mM imidazole, pH=8.0), disrupted by homogenization, centrifuged at 17,000 rpm, 4° C. for 20 minutes, and the supernatant was collected. (2) The proteins were bound using the Ni6FF affinity column, and washed with a washing buffer solution containing 20 mM imidazole (20 mM imidazole, 25 mM Tris, 200 mM NaCl, pH 8.0) to wash out impurity proteins, and the column is eluted with a solution containing 350 mM imidazole (350 mM imidazole, 25 mM Tris, 200 mM NaCl, pH 8.0) to obtain the protein of interest. (3) To the eluted protein sample, an appropriate amount of TEV protease having a His tag was added for digestion at 20° C. for 2 hours to obtain recombinant humanized type III collagen AT16. (4) The mixture of the enzymatically digested recombinant humanized type III collagen AT16 was dialyzed and buffer exchanged into sodium chloride solution, using a 10 kDa dialysis bag. (5) The buffer exchanged recombinant humanized type III collagen AT16 was concentrated to a protein concentration of not less than 10 mg/mL, using a 10 kDa ultrafiltration concentration tube.
6. The specific process for the formation of recombinant humanized type III collagen gel is that: the obtained recombinant humanized type III collagen AT16 was stored in a refrigerator, allowing the protein to be cross-linked at a low temperature environment to form a gel.
7. Detection of the purity of the recombinant type III humanized collagen gel.

The purity of the obtained AT16 protein was detected by SDS-PAGE. The specific process is that: 20 μL of the purified protein solution was taken and 5 μl of 5× protein loading buffer (250 mM of TrisHCl (pH 6.8), 10% SDS, 0.5% bromophenol blue, 50% glycerol, 5% β-mercaptoethanol) was added. The mixture was boiled in boiling water at 100° C. for 5 min, then added into SDS PAGE protein gel at 10 μl per well. After electrophoresis at 150 V for 1 h, the gel was stained with a Coomassie Brilliant Blue Stain (0.1% Coomassie Brilliant Blue R-250, 25% ethanol, 10% glacial acetic acid) for protein staining for 3 min, and then destained with a protein destaining solution (10% acetic acid, 5% ethanol).

FIG. 1 shows the electrophoresis detection results of the purified recombinant type III humanized collagen AT16. The apparent molecular weight of AT16 is 45 kDa, which corresponds to the theorical weight of the AT16 polypeptide, indicating the correct expression of the polypeptide AT16.

Example 2: Bioactivity Detection of the Recombinant Type III Humanized Collagen AT16

The collagen activity detection method may be available from the reference, Juming Yao, Satoshi Yanagisawa, Tetsuo Asakura, Design, Expression and Characterization of Collagen-Like Proteins Based on the Cell Adhesive and Crosslinking Sequences Derived from Native Collagens, J Biochem. 136, 643-649(2004). The specific implementation method is as follows:

(1) The concentrations of the protein samples to be tested, including bovine type I collagen standards (Sigma, cat. no.: 380002), and the recombinant type III humanized collagen AT16 provided by the present disclosure, were detected by ultraviolet absorption method.

Specifically, the UV absorption of the samples at 215 nm and 225 nm was measured respectively, and the protein concentrations were calculated using the empirical formula C(μg/mL)=144×(A215-A225). Note that it should be detected under the condition of A215<1.5. The principle of this method is to measure the characteristic absorption of peptide bonds under a far ultraviolet light, which is not affected by the content of chromophores. There are little interfering substances during the process of the method. The method is easy to operate, and is suitable for detecting human collagen and its analogues that are not colored by Coomassie brilliant blue. (reference: Walker JM. The Protein Protocols Handbook, second edition. HumanaPress. 43-45). After detection of the protein concentrations, the concentrations of all proteins to be tested were adjusted to 0.5 mg/mL with PBS.

(2) 100 μL of various protein solutions and blank PBS solution control were added into the 96-well plate respectively, and placed at room temperature for 60 minutes.

(3) 105 well-cultured 3T3 cells were added into each well and incubated at 37° C. for 60 min.

(4) Each well was washed 4 times with PBS.

(5) The absorbance at OD492 nm was detected with LDH detection kit (Roche, cat. no. 04744926001). The cell adhesion rate can be calculated relative to the value of the blank control. The calculation formula is as follows:

$$\text{cell adhesion rate} = \frac{\text{test well}-\text{blank well}}{\text{positive well}-\text{blank well}} \times 100\%.$$

The adhesion rate of cells can reflect the activity of collagen. The higher the activity of the protein, the better it can provide the cells with a high-quality external environment in a short time contributing to cell adherence.

Figure 2:
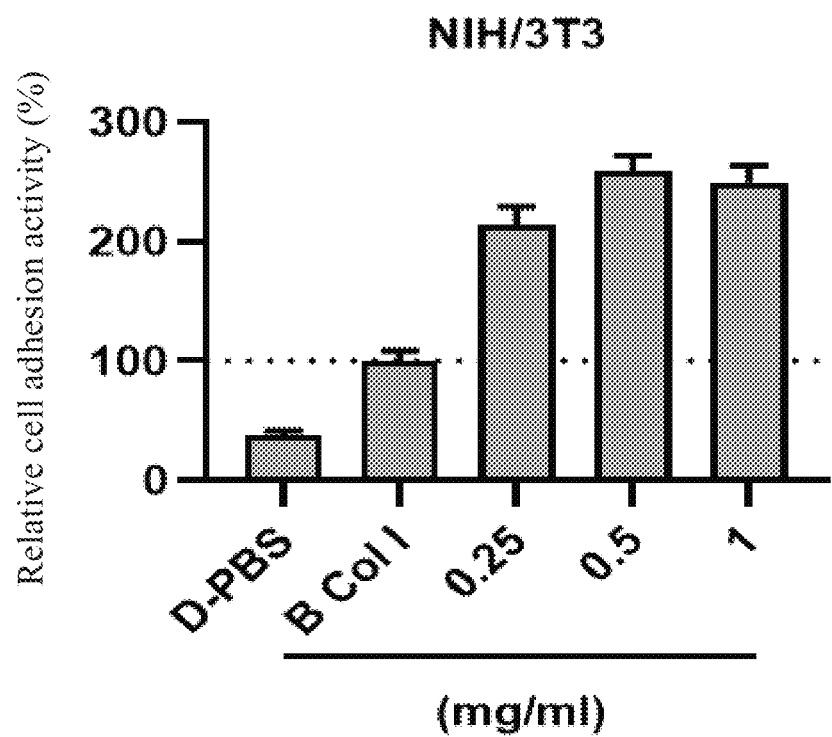
FIG. 2: Results of cell adhesion activity detection of the purified recombinant type III humanized collagen AT16.
Figure 3:
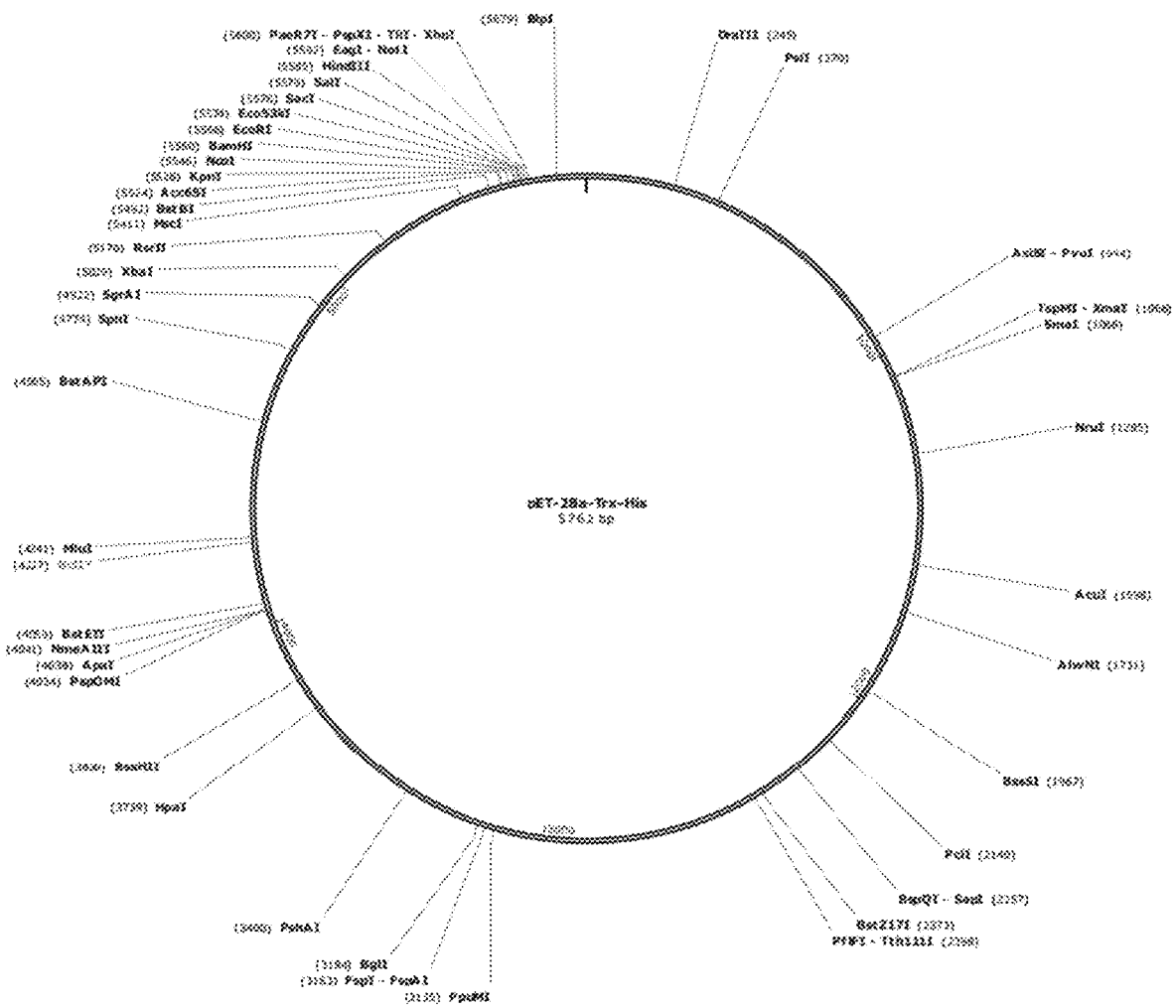
FIG. 3: Plasmid map.

The results are shown in FIG. 2 (D-PBS represents the blank PBS group; B *Col I* represents the bovine type I collagen standards control group; 0.25 represents the AT16 group at 0.25 mg/mL; 0.5 represents the AT16 group at 0.5 mg/mL; 1 represents the AT16 group at 1.0 mg/mL). It can be seen from the comparison that the various concentrations of the recombinant type III humanized collagen AT16 of the present disclosure have better bioadhesive activity, compared to the commercial human collagen.

Example 3: Mass Spectrometry of the Recombinant Type III Humanized Collagen AT16

| | Experimental method | | |
|---|---|---|---|
| Instrument Name | Matrix Assisted Laser Desorption Ionization - Time-of-Flight Mass Spectrometry MALDI-TOF/TOF Ultraflextreme ™, Brucker, Germany | | |
| Matrix | CHCA | Laser Energy | 125 |
| Data Search Software | Mascot | Search Species | ALL entries |
| Search Database | | NCBIprot | |

The protein samples were reduced with DTT and alkylated with iodoacetamide, and then digested with trypsin overnight. The peptide fragments obtained after enzymatical digestion were desalted with C18ZipTip, followed by mixed with matrix α-cyano-4-hydroxycinnamic acid (CHCA) and plated. Finally, the Matrix-Assisted Laser Desorption Ionization-Time-of-Flight Mass Spectrometer MALDI-TOF/TOF Ultraflextreme™, Brucker, Germany was used for analysis (for the technique of peptide fingerprinting, available from Protein J.2016; 35:212-7).

Data search was performed through the MS/MS Ion Search page from the local masco website. The protein identification results were obtained based on the primary mass spectrometry of the peptide fragments produced after enzymatical digestion. Detection parameters were: Trypsin digestion, with two missed cut sites. Alkylation of cysteine was set as a fixed modification, and oxidation of methionine as a variable modification. The database used for identification is NCBprot.

TABLE 1

Molecular Weights Detected by Mass Spectrometry and Corresponding Peptides

| Observed Value | Mr (Expected Value) | Peptide |
|---|---|---|
| 1093.5637 | 1092.5564 | GPAGPNGIPGEK (SEQ ID NO: 7) |
| 1660.8636 | 1659.8563 | GPAGPNGIPGEKGPAGER (SEQ ID NO: 8) |
| 1678.8907 | 1677.8834 | GAPGFRGPAGPNGIPGEK (SEQ ID NO: 9) |
| 2246.1276 | 2245.1203 | GAPGFRGPAGPNGIPGEKGPAGER (SEQ ID NO: 10) |

TABLE 1-continued

Molecular Weights Detected by Mass Spectrometry and Corresponding Peptides

The coverage rate of detected peptide fragments was 84.66%.

Example 4: Dynamic Viscometry of the Recombinant Type III Humanized Collagen T16, TE16c, and AT16

Experimental Method

The recombinant type III human collagen T16 (the amino acid sequence is GERGAPGFRGPAGPN-GIPGEKGPAGERGAPGERGAPGFRGPAGPNGIPGE KGPAGERGAPGERGAPGFRGPAGPN-GIPGEKGPAGERGAPGERGAPGFRG PAGPN-GIPGEKGPAGERGAPRSGERGAPGFRGPAGPN-GIPGEKGPAGERG APGERGAPGFRGPAGPNGIPGEKGPAGERGAPGER-GAPGFRGPAGPNGIP GEKGPAGERGAPGERGAPG-FRGPAGPNGIPGEKGPAGERGAPRSGERGAP GFRGPAGPNGIPGEKGPAGERGAPGERGAPG-FRGPAGPNGIPGEKGPAGE RGAPGERGAPG-FRGPAGPNGIPGEKGPAGERGAPGERGAPG-FRGPAGPNG IPGEKGPAGERGAPRSGERGAPGFRGPAGPN-GIPGEKGPAGERGAPGERG APGFRGPAGPN-GIPGEKGPAGERGAPGERGAPGFRGPAGPN-GIPGEKGPA GERGAPGERGAPGFRGPAGPNGIPGEKGPAGER-GAPRSGPPGPCCGGG, SEQ ID NO:5) and TE16c (the amino acid sequence is GERGAPGFRGPAGPN-GIPGEKGPAGERGAPGERGAPGFRGPAGPNGIPGE KGPAGERGAPGERGAPGFRGPAGPN-GIPGEKGPAGERGAPGERGAPGFRG PAGPN-GIPGEKGPAGERGAPGERGAPGFRGPAGPN-GIPGEKGPAGERGAP GERGAPGFRGPAGPNGIPGEKGPAGERGAPGER-GAPGFRGPAGPNGIPGE KGPAGERGAPGERGAPG-FRGPAGPNGIPGEKGPAGERGAPGERGAPGFRG PAGPNGIPGEKGPAGERGAPGERGAPGFRGPAGPN-GIPGEKGPAGERGAP GERGAPGFRGPAGPNGIPGE KGPAGERGAPGERGAPGFRGPAGPN-GIPGEKGPAGERGAPGERGAPGFRG PAGPN-GIPGEKGPAGERGAPGERGAPGFRGPAGPN-GIPGEKGPAGERGAP GERGAPGFRGPAGPNGIPGEKGPAGERGAP, SEQ ID NO:6) as well as the recombinant type III humanized collagen AT16 of the present disclosure at the same concentration and in corresponding solution (150 mM NaCl solution, polypeptide concentration 15 mg/mL) were stored in the environment of 2-8° C. respectively and put into the instrument rotational viscometer, in which the dynamic viscosity was tested for comparison.

Experimental Results

Figure 4:
FIG. 4: The image during dynamic viscometry of the human collagens T16, TE16c and AT16.

The dynamic viscosities of the recombinant type III humanized collagen T16 and TE16c are unmeasurable, while the measured dynamic viscosity of the recombinant type III humanized collagen AT16 of the present disclosure is 3510 mpa·s. This shows that the recombinant type III humanized collagen AT16 of the present disclosure is able to form a gel better under the same conditions, as shown in FIG. 4. According to FIG. 4, compared to the T16 and TE16c which are colorless and transparent, the AT16 is milky white and is able to form a gel.

Example 5: Purification and Preparation of AT4, AT8, AT12, AT16, and AT20 Proteins The AT4, AT8, AT12, AT16, AT20 proteins were prepared and purified as described in Example 1, wherein the number of repeating units of AT4 (gergapgfrgpagpngipgekgpagergap, SEQ ID NO: 1) is 4; the number of repeating units of AT8 is 8; the number of repeating units of AT12 (gergapgfrgpagpngipgekgpagergap, SEQ ID NO: 1) is 12; the number of repeating units of AT16 is 16; and the number of repeating units of AT20 protein is 20.

The specific sequences are as follows:

```
The amino acid sequence of AT4
                                          (SEQ ID NO: 11)
Gergapgfrgpagpngipgekgpagergapgergapgfrgpagpngipge kgpagergapgergapgfrgpagpngipgekgpagergapgergapgfrg pagpngipgekgpagergapgapgpccgg The corresponding optimized base sequence
                                          (SEQ ID NO: 12)
GGAGAAAGGGGGCGCCTGGCTTTCGTGGTCCGGCGGGTCCGAATGGCAT

TCCGGGTGAAAAGGGTCCTGCCGGTGAGCGTGGTGCTCCGGGTGAGCGCG

GCGCTCCGGGTTTCGCGGTCCCGCGGGTCCGAACGGCATCCCGGGAGAA

AAAGGCCCAGCTGGCGAGCGCGGTGCACCGGGCGAACGTGGTGCCCCGGG

CTTCCGTGGCCCAGCGGGTCCGAACGGTATTCCGGGCGAGAAAGGTCCGG

CAGGTGAACGTGGTGCGCCAGGCGAGCGTGGTGCGCCTGGTTTCAGAGGC

CCAGCAGGCCCAAATGGCATCCCCGGTGAGAAGGGCCCAGCCGGTGAGCG

CGGGGCACCGGGAGCGCCTGGTCCGTGTTGCGGTGGT

The amino acid sequence of AT8
                                          (SEQ ID NO: 13)
Gergapgfrgpagpngipgekgpagergapgergapgfrgpagpngipge kgpagergapgergapgfrgpagpngipgekgpagergapgergapgfrg pagpngipgekgpagergapgergapgfrgpagpngipgekgpagergap gergapgfrgpagpngipgekgpagergapgergapgfrgpagpngipge kgpagergapgergapgfrgpagpngipgekgpagergapgapgpccgg The corresponding optimized base sequence
                                          (SEQ ID NO: 14)
GGAGAAAGGGGGCGCCTGGCTTTCGTGGTCCGGCGGGTCCGAATGGCAT

TCCGGGTGAAAAGGGTCCTGCCGGTGAGCGTGGTGCTCCGGGTGAGCGCG

GCGCTCCGGGTTTCGCGGTCCCGCGGGTCCGAACGGCATCCCGGGAGAA

AAAGGCCCAGCTGGCGAGCGCGGTGCACCGGGCGAACGTGGTGCCCCGGG

CTTCCGTGGCCCAGCGGGTCCGAACGGTATTCCGGGCGAGAAAGGTCCGG

CAGGTGAACGTGGTGCGCCAGGCGAGCGTGGTGCGCCTGGTTTCAGAGGC

CCAGCAGGCCCAAATGGCATCCCCGGTGAGAAGGGCCCAGCCGGTGAGCG

CGGGGCACCGGGTGAACGTGGCGCGCCGGGCTTTCGCGGACCGGCGGGTC

CGAACGGCATCCCGGGTGAGAAGGGTCCGGCTGGCGAGCGTGGTGCGCCG

GGTGAACGTGGTGCACCGGGATTCCGCGGCCCGGCGGGACCGAATGGTAT

TCCGGGTGAGAAGGGTCCGGCGGGCGAACGCGGAGCACCAGGCGAACGCG

GCGCTCCGGGCTTTCGCGGTCCGGCGGGTCCGAATGGTATCCCGGGCGAG

AAGGGTCCTGCCGGTGAGCGTGGTGCCCCGGGCGAACGTGGCGCTCCGGG

TTTTCGTGGTCCGGCGGGTCCGAACGGCATTCCGGGTGAAAAGGGCCCAG

CGGGTGAGCGTGGCGCGCCAGGAGCGCCTGGTCCGTGTTGCGGTGGT

The amino acid sequence of AT12
                                          (SEQ ID NO: 15)
gergapgfrgpagpngipgekgpagergapgergapgfrgpagpngipge kgpagergapgergapgfrgpagpngipgekgpagergapgergapgfrg pagpngipgekgpagergapgergapgfrgpagpngipgekgpagergap gergapgfrgpagpngipgekgpagergapgergapgfrgpagpngipge kgpagergapgergapgfrgpagpngipgekgpagergapgergapgfrg pagpngipgekgpagergapgergapgfrgpagpngipgekgpagergap gergapgfrgpagpngipgekgpagergapgergapgfrgpagpngipge kgpagergapgapgpccgg The corresponding optimized base sequence
                                          (SEQ ID NO: 16)
GGAGAAAGGGGGCGCCTGGCTTTCGTGGTCCGGCGGGTCCGAATGGCAT

TCCGGGTGAAAAGGGTCCTGCCGGTGAGCGTGGTGCTCCGGGTGAGCGCG

GCGCTCCGGGTTTCCGCGGTCCCGCGGGTCCGAACGGCATCCCGGGAGAA

AAAGGCCCAGCTGGCGAGCGCGGTGCACCGGGCGAACGTGGTGCCCCGGG

CTTCCGTGGCCCAGCGGGTCCGAACGGTATTCCGGGCGAGAAAGGTCCGG

CAGGTGAACGTGGTGCGCCAGGCGAGCGTGGTGCGCCTGGTTTCAGAGGC

CCAGCAGGCCCAAATGGCATCCCCGGTGAGAAGGGCCCAGCCGGTGAGCG

CGGGGCACCGGGTGAACGTGGCGCGCCGGGCTTTCGCGGACCGGCGGGTC

CGAACGGCATCCCGGGTGAGAAGGGTCCGGCTGGCGAGCGTGGTGCGCCG

GGTGAACGTGGTGCACCGGGATTCCGCGGCCCGGCGGGACCGAATGGTAT

TCCGGGTGAGAAGGGTCCGGCGGGCGAACGCGGAGCACCAGGCGAACGCG

GCGCTCCGGGCTTTCGCGGTCCGGCGGGTCCGAATGGTATCCCGGGCGAG

AAGGGTCCTGCCGGTGAGCGTGGTGCCCCGGGCGAACGTGGCGCTCCGGG

TTTTCGTGGTCCGGCGGGTCCGAACGGCATTCCGGGTGAAAAGGGCCCAG

CGGGTGAGCGTGGCGCGCCAGGCGAGAGAGGTGCCCCGGGTTTTCGTGGC

CCGGCGGGTCCGAACGGCATCCCGGGTGAGAAAGGCCCGGCGGGCGAACG

TGGTGCGCCAGGCGAGAGAGGTGCTCCGGGTTTCCGTGGCCCGGCTGGTC

CGAACGGTATTCCGGGTGAAAAGGGCCCGGCGGGCGAGCGTGGCGCGCCG

GGTGAGCGTGGTGCCCCAGGCTTTCGTGGTCCAGCTGGTCCGAACGGTAT

CCCGGGTGAAAAAGGTCCGGCGGGTGAGCGTGGCGCGCCGGGTGAACGTG
```

-continued

GTGCCCAGGCTTCCGCGGGCCGGCAGGTCCCAACGGTATCCCGGGCGAG

AAAGGTCCGGCTGGCGAGCGAGGTGCCCCGGGAGCGCCTGGTCCGTGTTG

CGGTGGT

The amino acid sequence of AT16
(SEQ ID NO: 3)
gergapgfrgpagpngipgekgpagergapgergapgfrgpagpngipge kgpagergapgergapgfrgpagpngipgekgpagergapgergapgfrg pagpngipgekgpagergapgergapgfrgpagpngipgekgpagergap gergapgfrgpagpngipgekgpagergapgergapgfrgpagpngipge kgpagergapgergapgfrgpagpngipgekgpagergapgergapgfrg pagpngipgekgpagergapgergapgfrgpagpngipgekgpagergap gergapgfrgpagpngipgekgpagergapgergapgfrgpagpngipge kgpagergapgergapgfrgpagpngipgekgpagergapgergapgfrg pagpngipgekgpagergapgergapgfrgpagpngipgekgpagergap gergapgfrgpagpngipgekgpagergapgapgpccgg The corresponding optimized base sequence
(SEQ ID NO: 4)
GGAGAAAGGGGGCGCCTGGCTTTCGTGGTCCGGCGGGTCCGAATGGCAT

TCCGGGTGAAAAGGGTCCTGCCGGTGAGCGTGGTGCTCCGGGTGAGCGCG

GCGCTCCGGGTTTCCGCGGTCCCGCGGGTCCGAACGGCATCCCGGGAGAA

AAAGGCCCAGCTGGCGAGCGCGGTGCACCGGGCGAACGTGGTGCCCCGGG

CTTCCGTGGCCCAGCGGGTCCGAACGGTATTCCGGGCGAGAAAGGTCCGG

CAGGTGAACGTGGTGCGCCAGGCGAGCGTGGTGCGCCTGGTTTCAGAGGC

CCAGCAGGCCCAAATGGCATCCCCGGTGAGAAGGGCCCAGCCGGTGAGCG

CGGGGCACCGGGTGAACGTGGCGCGCCGGGCTTTCGCGGACCGGCGGGTC

CGAACGGCATCCCGGGTGAGAAGGGTCCGGCTGGCGAGCGTGGTGCGCCG

GGTGAACGTGGTGCACCGGGATTCCGCGGCCCGGCGGGACCGAATGGTAT

TCCGGGTGAGAAGGGTCCGGCGGGCGAACGCGGAGCACCAGGCGAACGCG

GCGCTCCGGGCTTTCGCGGTCCGGCGGGTCCGAATGGTATCCCGGGCGAG

AAGGGTCCTGCCGGTGAGCGTGGTGCCCCGGGCGAACGTGGCGCTCCGGG

TTTTCGTGGTCCGGCGGGTCCGAACGGCATTCCGGGTGAAAAGGCCCAG

CGGGTGAGCGTGGCGCGCCAGGCGAGAGAGGTGCCCCGGGTTTTCGTGGC

CCGGCGGGTCCGAACGGCATCCCGGGTGAGAAGGCCCGGCGGGCGAACG

TGGTGCGCCAGGCGAGAGAGGTGCTCCGGGTTTCCGTGGCCCGGCTGGTC

CGAACGGTATTCCGGGTGAAAAGGGCCCGGCGGGCGAGCGTGGCGCGCCG

GGTGAGCGTGGTGCCCCAGGCTTTCGTGGTCCAGCTGGTCCGAACGGTAT

CCCGGGTGAAAAGGTCCGGCGGGTGAGCGTGGCGCGCCGGGTGAACGTG

GTGCCCAGGCTTCCGCGGGCCGGCAGGTCCCAACGGTATCCCGGGCGAG

AAAGGTCCGGCTGGCGAGCGAGGTGCCCCGGGCGAACGTGGCGCGCCGGG

CTTCCGCGGTCCGGCAGGCCCGAACGGTATCCCGGGCGAGAAAGGTCCGG

CAGGTGAGCGTGGTGCGCCGGGTGAACGCGGCGCTCCGGGTTTTCGTGGC

CCGGCAGGCCCAAATGGCATTCCGGGCGAAAAAGGCCCAGCGGGTGAGCG

TGGTGCCCCGGGTGAGCGCGGTGCGCCGGGTTTCCGCGGTCCGGCGGGTC

CGAATGGTATTCCGGGCGAAAAAGGCCCGGCGGGCGAGCGTGGCGCTCCG

GGCGAACGTGGAGCGCCAGGATTCCGCGGCCCGGCAGGACCGAACGGCAT

CCCGGGAGAAAAGGGCCCGGCGGGTGAACGTGGTGCACCGGGAGCGCCTG

GTCCGTGTTGCGGTGGT

The amino acid sequence of AT20
(SEQ ID NO: 17)
gergapgfrgpagpngipgekgpagergapgergapgfrgpagpngipge kgpagergapgergapgfrgpagpngipgekgpagergapgergapgfrg pagpngipgekgpagergapgergapgfrgpagpngipgekgpagergap gergapgfrgpagpngipgekgpagergapgergapgfrgpagpngipge kgpagergapgergapgfrgpagpngipgekgpagergapgergapgfrg pagpngipgekgpagergapgergapgfrgpagpngipgekgpagergap gergapgfrgpagpngipgekgpagergapgergapgfrgpagpngipge kgpagergapgergapgfrgpagpngipgekgpagergapgergapgfrg pagpngipgekgpagergapgergapgfrgpagpngipgekgpagergap gergapgfrgpagpngipgekgpagergapgergapgfrgpagpngipge kgpagergapgergapgfrgpagpngipgekgpagergapgergapgfrg pagpngipgekgpagergapgergapgfrgpagpngipgekgpagergap gapgpccgg The corresponding optimized base sequence
(SEQ ID NO: 18)
GGAGAAAGGGGGCGCCTGGCTTTCGTGGTCCGGCGGGTCCGAATGGCAT

TCCGGGTGAAAAGGGTCCTGCCGGTGAGCGTGGTGCTCCGGGTGAGCGCG

GCGCTCCGGGTTTCCGCGGTCCCGCGGGTCCGAACGGCATCCCGGGAGAA

AAAGGCCCAGCTGGCGAGCGCGGTGCACCGGGCGAACGTGGTGCCCCGGG

CTTCCGTGGCCCAGCGGGTCCGAACGGTATTCCGGGCGAGAAAGGTCCGG

CAGGTGAACGTGGTGCGCCAGGCGAGCGTGGTGCGCCTGGTTTCAGAGGC

CCAGCAGGCCCAAATGGCATCCCCGGTGAGAAGGGCCCAGCCGGTGAGCG

CGGGGCACCGGGTGAACGTGGCGCGCCGGGCTTTCGCGGACCGGCGGGTC

CGAACGGCATCCCGGGTGAGAAGGGTCCGGCTGGCGAGCGTGGTGCGCCG

GGTGAACGTGGTGCACCGGGATTCCGCGGCCCGGCGGGACCGAATGGTAT

TCCGGGTGAGAAGGGTCCGGCGGGCGAACGCGGAGCACCAGGCGAACGCG

GCGCTCCGGGCTTTCGCGGTCCGGCGGGTCCGAATGGTATCCCGGGCGAG

AAGGGTCCTGCCGGTGAGCGTGGTGCCCCGGGCGAACGTGGCGCTCCGGG

TTTTCGTGGTCCGGCGGGTCCGAACGGCATTCCGGGTGAAAAGGGCCCAG

CGGGTGAGCGTGGCGCGCCAGGCGAGAGAGGTGCCCCGGGTTTTCGTGGC

CCGGCGGGTCCGAACGGCATCCCGGGTGAGAAAGGCCCGGCGGGCGAACG

TGGTGCGCCAGGCGAGAGAGGTGCTCCGGGTTTCCGTGGCCCGGCTGGTC

CGAACGGTATTCCGGGTGAAAAGGGCCCGGCGGGCGAGCGTGGCGCGCCG

GGTGAGCGTGGTGCCCCAGGCTTTCGTGGTCCAGCTGGTCCGAACGGTAT

CCCGGGTGAAAAGGTCCGGCGGGTGAGCGTGGCGCGCCGGGTGAACGTG

GTGCCCCAGGCTTCCGCGGGCCGGCAGGTCCCAACGGTATCCCGGGCGAG

-continued

```
AAAGGTCCGGCTGGCGAGCGAGGTGCCCCGGGCGAACGTGGCGCGCCGGG

CTTCCGCGGTCCGGCAGGCCCGAACGGTATCCCGGGCGAGAAAGGTCCGG

CAGGTGAGCGTGGTGCGCCGGGTGAACGCGGCGCTCCGGGTTTTCGTGGC

CCGGCAGGCCCAAATGGCATTCCGGGCGAAAAAGGCCCAGCGGGTGAGCG

TGGTGCCCCGGGTGAGCGCGGTGCGCCGGGTTTCCGCGGTCCGGCGGGTC

CGAATGGTATTCCGGGCGAAAAAGGCCCGGCGGGCGAGCGTGGCGCTCCG

GGCGAACGTGGAGCGCCAGGATTCCGCGGCCCGGCAGGACCGAACGGCAT

CCCGGGAGAAAAGGGCCCGGCGGGTGAACGTGGTGCACCGGGAGAAAGGG

GGGCGCCTGGCTTTCGTGGTCCGGCGGGTCCGAATGGCATTCCGGGTGAA

AAGGGTCCTGCCGGTGAGCGTGGTGCTCCGGGTGAGCGCGGCGCTCCGGG

TTTCCGCGGTCCCGCGGGTCCGAACGGCATCCCGGGAGAAAAAGGCCCAG

CTGGCGAGCGCGGTGCACCGGGCGAACGTGGTGCCCCGGGCTTCCGTGGC

CCAGCGGGTCCGAACGGTATTCCGGGCGAGAAAGGTCCGGCAGGTGAACG

TGGTGCGCCAGGCGAGCGTGGTGCGCCTGGTTTCAGAGGCCCAGCAGGCC

CAAATGGCATCCCCGGTGAGAAGGGCCCAGCCGGTGAGCGCGGGGCACCG

GGAGCGCCTGGTCCGTGTTGCGGTGGT.
```

Example 6: SDS-PAGE Experiment of AT4, AT8, AT12, AT16, and AT20

Experimental process: 20 µL of the purified protein solution was taken and to the protein solution, 5 µl of 5× protein loading buffer (250 mM Tris HCl (pH 6.8), 10% SDS, 0.5% bromophenol blue, 50% glycerol, 5% β-mercaptoethanol) was added. The mixture was boiled in boiling water at 100° C. for 5 min, then added into SDS PAGE protein gel at 10 µl per well. After electrophoresis at 150 V for 1 h, the gel was stained with a Coomassie Brilliant Blue Stain (0.1% Coomassie Brilliant Blue R 250, 25% ethanol, 10% glacial acetic acid) for protein staining for 3 min, and then destained with a protein destaining solution (10% acetic acid, 5% ethanol).

Experimental Results

Figure 5:
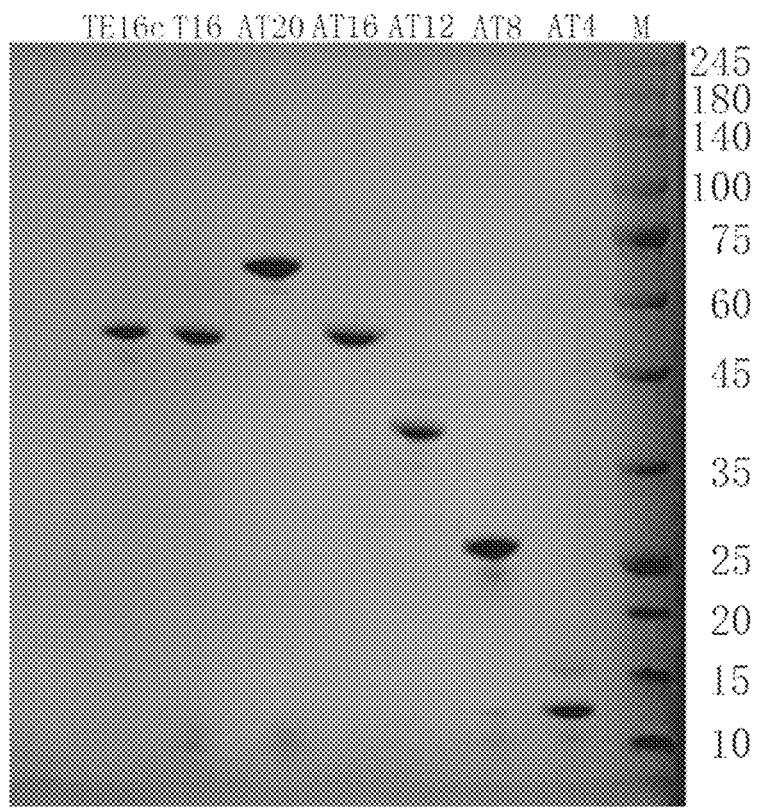
FIG. 5: Electrophoresis detection results of the purified recombinant type III humanized collagens AT4, AT8, AT12, AT16, and AT20.

FIG. 5 shows the electrophoresis detection results of the purified recombinant type III humanized collagens AT4, AT8, AT12, AT16 and AT20. The apparent molecular weights of AT4, AT8, AT12, AT16 and AT20 are 13 kDa, 26 kDa, 38 kDa, 45 kDa, and 66 kDa, respectively, and the molecular weights correspond to theorical weights of AT4, AT8, AT12, AT16, and AT20 polypeptides respectively, indicating that AT4, AT8, AT12, AT16, and AT20 polypeptides are correctly expressed.

Example 7: Bioactivity Detection of AT4, AT8, AT12, AT16, and AT20 Experimental Process The collagen activity detection method may be available from the reference, Juming Yao, Satoshi Yanagisawa, Tetsuo Asakura, Design, Expression and Characterization of Collagen-Like Proteins Based on the Cell Adhesive and Cross-linking Sequences Derived from Native Collagens, J Biochem. 136, 643-649(2004). The specific implementation method is as follows:

(1) The concentrations of the protein samples to be tested, including bovine type I collagen standards (Sigma, no.: 380002), and the recombinant type III humanized collagens AT4, AT8, AT12, AT16, and AT20 provided by the present disclosure, were detected by ultraviolet absorption method.

Specifically, the UV absorption of the samples at 215 nm and 225 nm was measured respectively, and the protein concentrations were calculated using the empirical formula C(µg/mL)=144×(A215-A225). Note that it should be detected under the condition of A215<1.5. The principle of this method is to measure the characteristic absorption of peptide bonds under a far ultraviolet light, which is not affected by the content of chromophores. The method has little interfering substances, and is easy to operate, and is suitable for detecting human collagen and its analogues that are not colored by Coomassie brilliant blue. (Reference: Walker JM. The Protein Protocols Handbook, second edition. HumanaPress. 43-45). After detection of the protein concentrations, the concentrations of all proteins to be tested were adjusted to 0.5 mg/mL with PBS.

(2) 100 µL of various protein solutions and blank PBS solution control were added into the 96-well plate respectively, and placed at room temperature for 60 minutes.

(3) 105 well-cultured 3T3 cells were added into each well and incubated at 37° C. for 60 min.

(4) Each well was washed 4 times with PBS.

(5) The absorbance at OD492 nm was detected with LDH detection kit (Roche, cat. no. 04744926001). The cell adhesion rate can be calculated according to the value of the blank control. The calculation formula is as follows:

$$\text{cell adhesion rate} = \frac{\text{test well} - \text{blank well}}{\text{positive well} - \text{blank well}} \times 100\%.$$

The adhesion rate of cells can reflect the activity of collagen. The higher the activity of the protein, the better it can provide the cells with a high-quality external environment in a short time contributing to cell adherence.

Experimental Results

Figure 6:
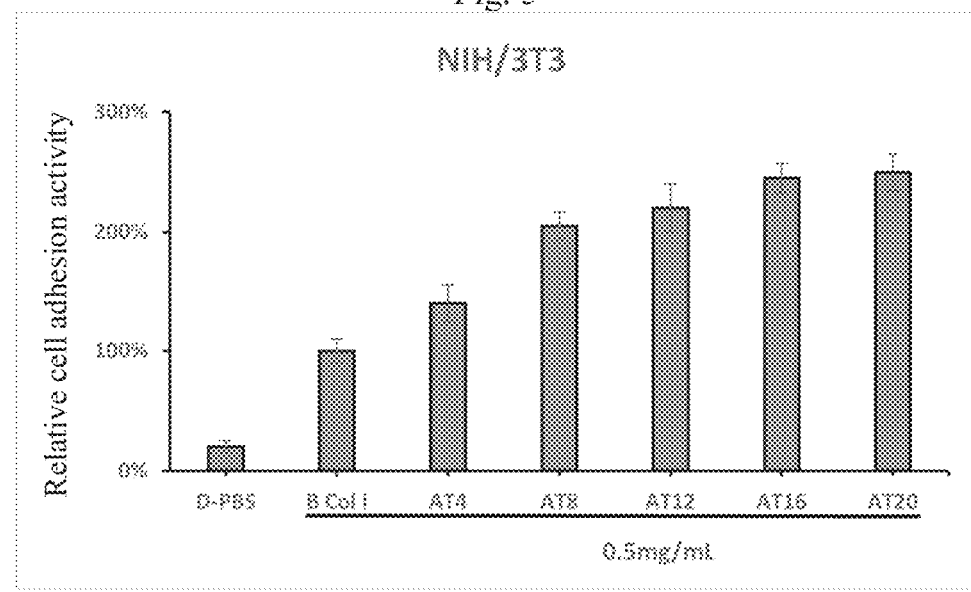
FIG. 6: The bioadhesive activity of test samples AT4, AT8, AT12, AT16, and AT20.

The results are shown in FIG. 6 (D-PBS represents the blank PBS group; B Col I represents the bovine type I collagen standards control group; the concentrations of test samples AT4, AT8, AT12, AT16, and AT20 are respectively 0.5 mg/mL). It can be seen from the comparison that the recombinant type III humanized collagen AT4, AT8, AT12, AT16 and AT20 of the present disclosure all have excellent bioadhesive activities at the concentration of 0.5 mg/mL, compared to commercial human collagen.

Example 8: Mass Spectrometry of AT4, AT8, AT12, and AT20 Experimental Method

| Instrument Name | Matrix Assisted Laser Desorption Ionization - Time-of-Flight Mass Spectrometry MALDI-TOF/TOF Ultraflextreme ™, Brucker, Germany | | |
|---|---|---|---|
| Matrix | CHCA | Laser Energy | 125 |
| Data Search Software | Mascot | Search Species | ALL entries |
| Search Database | | NCBIprot | |

The protein samples were reduced with DTT and alkylated with iodoacetamide, and then digested with trypsin overnight. The peptide fragments obtained after enzymatical digestion were desalted with C18ZipTip, followed by mixed with matrix α-cyano-4-hydroxycinnamic acid (CHCA) and plated. Finally, the Matrix-Assisted Laser Desorption Ionization-Time-of-Flight Mass Spectrometer MALDI-TOF/TOF Ultraflextreme™, Brucker, Germany was used for analysis (for the technique of peptide fingerprinting, available from Protein J.2016; 35:212-7).

Data search is conducted through the MS/MS Ion Search page from the local masco website. The protein identification results were obtained based on the primary mass spectrometry of the peptide fragments produced after enzymatical digestion. Detection parameters were: Trypsin digestion, with two missed cut sites. Alkylation of cysteine was set as a fixed modification, and oxidation of methionine as a variable modification. The database used for identification is NCBprot.

Experimental Results

| Observed Value | Mr (Expected Value) | Peptide |
|---|---|---|
| AT4 Molecular Weights Detected by Mass Spectrometry and Corresponding Peptides | | |
| 839.8683 | 839.8528 | GPAGERGA (SEQ ID NO: 19) |
| 1337.4579 | 1337.4432 | GFRGPAGPNGIP (SEQ ID NO: 20) |
| 1765.8265 | 1765.8446 | GERGAPGERGAPGFR (SEQ ID NO: 21) |
| 2413.5765 | 2413.5232 | EKGPAGERGAPGERGAPGFRG (SEQ ID NO: 22) |
| AT8 Molecular Weights Detected by Mass Spectrometry and Corresponding Peptides | | |
| 1087.1974 | 1087.1434 | GPNGIPGEKG (SEQ ID NO: 23) |
| 1497.5287 | 1497.5728 | KGPAGERGAPGER (SEQ ID NO: 24) |
| 1602.6752 | 1602.6600 | PAGPNGIPGEKGPAGE (SEQ ID NO: 25) |
| 2452.5278 | 2452.5542 | AGPNGIPGEKGPAGERGAPGER (SEQ ID NO: 26) |
| AT12 Molecular Weights Detected by Mass Spectrometry and Corresponding Peptides | | |
| 913.9889 | 913.9748 | ERGAPGFRGP (SEQ ID NO: 27) |
| 1442.5276 | 1442.5364 | RGAPGERGAPGFR (SEQ ID NO: 28) |
| 1570.6602 | 1570.6612 | GPAGPNGIPGEKGPA (SEQ ID NO: 29) |
| 2527.6376 | 2527.6212 | NGIPGEKGPAGERGAPGERGAPG (SEQ ID NO: 30) |
| AT20 Molecular Weights Detected by Mass Spectrometry and Corresponding Peptides | | |
| 1070.1833 | 1070.1130 | PAGPNGIPGE (SEQ ID NO: 31) |
| 1559.6287 | 1559.6406 | GFRGPAGPNGIPGE (SEQ ID NO: 32) |
| 2013.1492 | 2013.1382 | RGAPGERGAPGFRGPAGP (SEQ ID NO: 33) |
| 2686.8492 | 2686.8516 | PGERGAPGFRGPAGPNGIPGEKGP (SEQ ID NO: 34) |

Example 9: Viscosity Testing of AT4, AT8, AT 12, AT 16, and AT20 Experiment Process The recombinant type III humanized collagens AT4, AT8, AT12, AT16, and AT20 of the present disclosure at the same concentration and in corresponding solution (150 mM NaCl solution, polypeptide concentration 15 mg/mL) were stored in the environment of 2-8° C. respectively and put into the instrument rotational viscometer, in which the dynamic viscosity was tested for comparison.

Experimental Results

Figure 7:
FIG. 7: The image of gels formed by the recombinant type III humanized collagens AT4, AT8, AT12, AT16, and AT20.

The dynamic viscosities of the recombinant type III humanized collagens T16 and TE16c are unmeasurable, while the measured dynamic viscosities of the recombinant type III humanized collagen AT4, AT8, AT12, AT16 and AT20 of the present disclosure are 3225 mpa·s, 3340 mpa·s, 3475 mpa·s, 3510 mpa·s, and 3650 mpa·s, respectively. This shows that the recombinant type III humanized collagens AT4, AT8, AT12, AT16 and AT20 of the present disclosure are able to form gels better under the same conditions, as shown in FIG. 7. According to FIG. 7, compared to T16 and TE16c which are colorless and transparent, AT4, AT8, AT12, AT16 and AT20 are milky white and are able to form gels.

The invention claimed is:

1. A polypeptide consisting of an N-terminal sequence and a C-terminal sequence, wherein the N-terminal sequence consists of repeating units, wherein the repeating unit consists of the amino acid sequence of SEQ ID NO:1, wherein the C-terminal sequence consists of the amino acid sequence of SEQ ID NO:2, wherein the N-terminal sequence and the C-terminal sequence are directly linked, wherein each repeating unit is directly linked, and wherein the number of the repeating units is 4-20.

2. A composition comprising the polypeptide according to claim 1.

3. The polypeptide of claim 1, which consists of the amino acid sequence of SEQ ID NO: 3.

4. A gel comprising the polypeptide according to claim 1.

5. The gel according to claim 4, wherein the gel does not comprise a cross-linking agent.

6. A polynucleotide encoding the polypeptide according to claim 1.

7. The polynucleotide according to claim 6, consisting of the nucleotide sequence of SEQ ID NO:4.

8. A nucleic acid consisting of the polynucleotide according to claim 6 and a nucleotide sequence encoding a purification tag or a nucleotide sequence encoding a leader sequence.

9. The nucleic acid according to claim 8, wherein the purification tag is a His tag, a GST tag, an MBP tag, a SUMO tag, or a NusA tag.

10. A vector comprising the polynucleotide according to claim 6.

11. A host cell comprising the polynucleotide according to claim 6.

12. The host cell according to claim 11, wherein the host cell is a bacterium, a fungus, or an animal cell.

13. The host cell according to claim 12, wherein the bacterium is *E. coli* and the fungus is a yeast.

14. A method of producing a polypeptide, comprising:
(1) culturing the host cell according to claim 11 under a suitable culture condition;
(2) harvesting the host cell and/or the culture medium comprising the polypeptide; and
(3) purifying the polypeptide.

15. A method of preparing a gel, comprising the step of storing the polypeptide according to claim 1 at a temperature ranging from 2-8° C.

16. The method according to claim 15, wherein the polypeptide is a polypeptide in a sodium chloride solution.

17. A method for increasing cell adhesion, the method comprising administering to a subject the polypeptide according to claim 1, thereby increasing cell adhesion.

18. A method for performing tissue filling and/or augmentation, the method comprising administering to a subject the polypeptide according to claim 1, thereby performing tissue filling and/or augmentation.

19. A method for breast augmentation, rhinoplasty and/or facial filling, the method comprising administering to a subject the polypeptide according to claim 1, thereby performing breast augmentation, rhinoplasty and/or facial filling.

* * * * *